US006864074B2

(12) United States Patent
Yano et al.

(10) Patent No.: US 6,864,074 B2
(45) Date of Patent: Mar. 8, 2005

(54) DNA FRAGMENT CARRYING TOLUENE MONOOXYGENASE GENE, RECOMBINANT PLASMID, TRANSFORMED MICROORGANISM, METHOD FOR DEGRADING CHLORINATED ALIPHATIC HYDROCARBON COMPOUNDS AND AROMATIC COMPOUNDS, AND METHOD FOR ENVIRONMENTAL REMEDIATION

(75) Inventors: Tetsuya Yano, Atsugi (JP); Tsuyoshi Nomoto, Komae (JP); Takeshi Imamura, Chigasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/430,029

(22) Filed: Oct. 29, 1999

(65) Prior Publication Data

US 2002/0168738 A1 Nov. 14, 2002

(30) Foreign Application Priority Data

Oct. 30, 1998 (JP) .......................................... 10-310801

(51) Int. Cl.$^7$ ............................. C12N 9/02; C12N 1/21; C12N 15/52; C12P 1/00; C07H 21/04

(52) U.S. Cl. ...................... 435/189; 435/41; 435/252.3; 435/254.11; 435/320.1; 536/23.2; 536/23.7

(58) Field of Search ..................... 435/189, 41, 252.3, 435/254.11, 320.1, 252.34; 536/23.2, 23.7

(56) References Cited

U.S. PATENT DOCUMENTS

| | | | | |
|---|---|---|---|---|
| 4,877,736 A | 10/1989 | Fliermans | ................... | 435/183 |
| 4,925,802 A | 5/1990 | Nelson et al. | ............... | 435/262 |
| 5,316,940 A | 5/1994 | Georgiou et al. | ......... | 435/252.1 |
| 5,543,317 A | 8/1996 | Shields et al. | ........... | 435/240.2 |
| 6,472,191 B1 * | 10/2002 | Yano et al. | ................. | 435/189 |

FOREIGN PATENT DOCUMENTS

| | | |
|---|---|---|
| EP | 0447862 | 3/1990 |
| EP | 0597283 | 5/1994 |
| EP | 0611729 | 8/1994 |
| JP | 02-092274 | 4/1990 |
| JP | 03-292970 | 12/1991 |
| JP | 06-022769 | 2/1994 |
| JP | 06-070753 | 3/1994 |
| JP | 06-105691 | 4/1994 |
| JP | 07-123976 | 5/1995 |
| JP | 07-143882 | 6/1995 |
| JP | 07-236895 | 9/1995 |
| JP | 08-070881 | 3/1996 |
| JP | 08-294387 | 11/1996 |
| WO | WO 89/09827 | 10/1989 |
| WO | WO 90/06901 | 6/1990 |
| WO | WO 92/19738 | 11/1992 |

OTHER PUBLICATIONS

Winter et al., "Efficient Degradation . . . E. Coli", Bio/Technology, vol. 7, No, 15, pp. 282–285 (1989).
Ewers et al., Selection of TCE Degrading Bacteria . . . by TCE, Arch. Microbiol. (1990) 154:410–413.
Embley et al., Lactobacillus . . . Int'l. J. Sys. Bact., vol. 39, No. 3, Jul. 1989, pp. 368–370.
Hanson et al/. "Development of Methanothrops . . . Olefins," Am. Chem. Soc., Nat'l. Mtg, Div. Environ. Chem., Miami Beach, Sep. 10–19, 1989, pp. 365–367.
Negoro et al., "Growth of Microalgae . . . and NOx", vols. 28/27, 1991, pp. 877–886.
Henry et al., "Influence of Endogenous . . . Groundwater Acquifer", Appl. & Envir. vol. 57, No. 1 (1991), pp. 236–244.
Little et al.; "Tricholorethylene Biodegradation . . . Bacterium", Appl. & Environ. Microb., vol. 54, No. 4 (1988), pp. 951–956.
Shields et al., "Mutant of Pseudomonas . . . Trichloroethylene", Appl. & Environ. Microb., vol. 57, No. (1991), pp. 1935–1941.
Duba et al., "TCE Remediation . . . Bioaugmentation", Environ. Sci. Technol. 1996, 30, 1982–1989.
Baum et al., "Regulation of Insecticidal . . . Thuringiensis", Mol. Microb. (1995), 18 (i) 1–12.
Ng et al., "Cloning and sequences . . . P35X", Gene 151 (1994) 29–36.
Ng et al., "Aromatic Effector . . . Controls", J. Bacteriol. (1995) 177(6) 1485–1490.
Olsen et al., "A Novel Toluene . . . PKO1", J. Bacteriol. (1994) 176(12) 3749–3756.
Whited et al., Toluene–4–Monooxygenase . . . KR1, Bacteriol. (1991) 173(9) 3010–3016.
Nordlund et al., "Complete Nucleotide Sequence . . . CF 600", J. Bacteriol. (1990) 172(12) 6826–6833.
Johnson et al., "Nucleotide Sequence Analysis . . . JS150", Appl. & Environ. Microbiol. (1995) 61(9) 3336–3346.
Uchiyama et al., Aerobic Degradation of Trichloroethylene . . . Strain M, Agric. Biol. Chem. 53(11), 2903–2907, 1989.
Tsien et al., "Biodegradation of Trichloroethylene by . . . OB3b", Appl. Environ. Microbiol., 55, (12), 3155–3161 (1989).

(List continued on next page.)

*Primary Examiner*—Elizabeth Slobodyansky
(74) *Attorney, Agent, or Firm*—Fitzpatrick, Cella, Harper & Scinto

(57) ABSTRACT

A recombinant DNA is constructed by using a toluene monooxygenase gene isolated from Burkholderia cepacia strain KK01 and employed to provide the transformant which can express toluene monooxygenase useful for cleaning of aqueous media such as drain and waste water containing chlorinated aliphatic hydrocarbon compounds or aromatic compounds, for remediation of soil polluted with such compounds, and cleaning of air (gas phase) polluted with volatile organic chlorine compounds.

49 Claims, 1 Drawing Sheet

OTHER PUBLICATIONS

Wackett et al., "Survey of Microbiol. Oxugenases: . . . Bacteria", Appl. & Environ. Microbiol., 55 (11), 2960–2964 (1989).

Nelson et al., "Aerobic Metabolism of Trichloroethylene . . . Isolate", Appl. & Environ. Microbiol., 52 (2), 383–384 (1986).

Nelson et al., "Biodegradation of Trichloroethylene . . . Pathway", Appl. & Environ. Microbiol., 53 (5), 949–954.

Kamath et al., "New Pathway for the Biodegradation . . . niger", Appl. & Environ. Microbiol. 56, (1), 275–280.

Wackett et al., "Degradation of Trichloroethylene . . . F1", Appl. & Environ. Microbiol., 54, (7), 1703–1708 (1988).

Vandenbergh et al., "Metabolism of Volatile Chlorinated . . . fluorescens", Appl. & Environ. Microbiol., 54, (10), 2578–2579 (1988).

Vannelli et al., "Degradation of Halogenated . . . Nitrosomonas europaea", Appl. & Environ. Microbiol., 56, (4), 1169–1171 (1990).

Shields et al., "Selection of a Pseudomonas cepacia . . . Trichloroethylene", Appl. & Environ. Microbiol., 58, (12) 3977–3982 (1992).

Nakajima et al., "Novel Metabolite of Trichloroethylene . . . Pathway", Biosci. Biotech. Biochem., 56, (3), 486–489 (1992).

Nakajima et al., "Purification and Properties . . . Methylocystis", Biosci. Biotech. Biochem., 56, (5) 736–740 (1992).

Beam et al., "Microbiol. Degradation of . . . Commensalism", J. Gen. microbiol., 82, 163–169 (1974).

Journal of Japan Sewage Works Assoc., 24, (273), 27–32 (1987).

* cited by examiner

DNA FRAGMENT CARRYING TOLUENE MONOOXYGENASE GENE, RECOMBINANT PLASMID, TRANSFORMED MICROORGANISM, METHOD FOR DEGRADING CHLORINATED ALIPHATIC HYDROCARBON COMPOUNDS AND AROMATIC COMPOUNDS, AND METHOD FOR ENVIRONMENTAL REMEDIATION

BACKGROUND OF THE INVENTION

1. Field of the Invention

The present invention relates to a novel DNA fragment carrying a toluene monooxygenase gene, a novel recombinant DNA containing the DNA fragment, a transformant containing the recombinant DNA, and a method for degrading chlorinated aliphatic hydrocarbon compounds such as trichloroethylene (TCE) and dichloroethylene (DCE) and aromatic compounds such as toluene, benzene, phenol, and cresol. The present invention also relates to a method for environmental remediation useful for cleaning of aqueous media such as wastewater and effluent containing at least either a chlorinated aliphatic hydrocarbon compound or an aromatic compound and air (gas phase) and soil polluted with chlorinated aliphatic hydrocarbon compounds.

2. Related Background Art

Recently, it has become a serious problem the environmental pollution with volatile organic chlorinated compounds which are harmful to the organisms and hardly degradable. Especially, the soil in the industrial areas in Japan as well as abroad is considered to be contaminated with chlorinated aliphatic hydrocarbon compounds such as tetrachloroethylene (PCE), trichloroethylene (TCE), and dichloroethylene (DCE) and aromatic compounds such as toluene, benzene, phenol, and cresol. There have been a number of reports on actual detection of such pollutants through environmental surveys. It is supposed that these compounds remaining in soil dissolve in ground water via rainwater, and thereby spread over the surrounding areas. There is a strong suspicion that these compounds are carcinogens, and further, these are quite stable in the environment; therefore contamination of groundwater, which is used as a source of drinking water, has become a serious social problem. Therefore, cleaning of aqueous media such as contaminated groundwater and soil through removal and degradation of these compounds and accompanying cleaning of the surrounding gas phase are quite important in view of the environment protection. Technologies required for cleaning (for example, adsorption treatment using activated carbon, degradation treatment using light and heat) have been developed. Technologies presently available, however, are not always practical in terms of cost and operability. Recently, microbial degradation of chlorinated aliphatic hydrocarbon compounds such as TCE that is stable in environment has been reported. The microbial degradation method have advantages such as: (1) degradation of chlorinated aliphatic hydrocarbon compounds into harmless substances by using appropriately selected microorganism; (2) no requirement for any special chemicals in principle; and (3) reduction of the labor and costs of maintenance.

The examples of microorganisms capable of degrading TCE are as follows:

*Welchia alkenophila* sero 5 (U.S. Pat. No. 4,877,736, ATCC 53570, *Welchia alkenophila* sero 33 (U.S. Pat. No. 4,877,736, ATCC 53571), *Methylocystis* sp. Strain M (Agric. Biol. Chem., 53, 2903 (1989), Biosci. Biotech. Bichem., 56, 486 (1992), ibid. 56, 736 (1992)), *Methylosinus trichosporium* OB3b (Am. Chem. Soc. Natl. meet. Div. Environ. Microbiol., 29, 365 (1989), Appl. Environ. Microbiol., 55, 3155 (1989), Appl. Biochem. Biotechnol. 28, 877 (1991), Japanese Patent Application Laid-Open No. 2-92274 specification, Japanese Patent Laid-Open Application No. 3-292970), *Methylomonas* sp. MM2 (Appl. Environ. Microbiol., 57, 236 (1991), *Alcaligenes denitrificans* ssp. *Xylosoxidans* JE75 (Arch. Microbiol., 154, 410 (1990), *Alcaligenes eutrophus* 3 MP134 (Appl. Environ. Microbiol., 56, 1179 (1990), *Alcaligenes eutrophus* FERM-13761 (Japanese Patent Laid-Open Application No. 7-123976), *Pseudomonas aeruginosa* J1104 (Japanese Patent Application Laid-Open No. 7-236895), *Mycobacterium vaccae* JOB5 (J. Gen. Microbiol., 82, 163 (1974), Appl. Environ. Microbiol., 55, 2960 (1989), ATCC 29678), *Pseudomonas putida* BH (Gesuidou Kyoukai-shi (Japan Sewage Works Association Journal), 24, 27 (1987)), *Pseudomonas* sp. strain G4 (Appl. Environ. Microbiol., 52, 383 (1968), ibid. 53, 949 (1987), ibid. 54, 951 (1988), ibid. 56, 279 (1990), ibid. 57, 193 (1991), U.S. Pat. No. 4,925,802, ATCC 53617, this strain was first classified as *Pseudomonas cepacia* and then changed to *Pseudomonas* sp.), *Pseudomonas mendocia* KR-1 (Bio/Technol., 7, 282 (1989)), *Pseudomonas putida* F1 (Appl. Environ Microbiol., 54, 1703 (1988), ibid. 54, 2578 (1988)), *Pseudomonas fluorescens* PFL12 (Appl. Environ. Microbiol., 54, 2578 (1988)), *Pseudomonas putida* KWI-9 (Japanese Patent Application Laid-Open No. 6-70753), *Pseudomonas cepacia* KK01 (Japanese Patent Application Laid-Open No. 6-22769), *Nitrosomonas europaea* (Appl. Environ. Microbio., 56, 1169 (1990), *Lactobacillus vaginalis* sp. nov (Int. J. Syst. Bacteriol., 39, 368 (1989), ATCC 49540), *Nocardia corallina* B-276 (Japanese Patent Application Laid-Open No. 8-70881, FERM BP-5124, ATCC 31338), and so on.

The problem in actually using these degrading microorganisms in environmental remediation treatment, however, resides in optimizing and maintaining expression of their degradation activity for chlorinated aliphatic hydrocarbon compounds such as TCE. In an environmental remediation treatment which utilizes phenol, toluene, methane, or the like as an inducer, continuous supply of the inducer is indispensable, since depletion of such inducers directly results in stoppage of degradation of chlorinated aliphatic hydrocarbon compounds. Presence of such inducers, on the other hand, may inhibit the efficient degradation of the target substance such as TCE, since the affinity of the chlorinated aliphatic hydrocarbon compounds such as TCE as a substrate is considerably low in comparison with these inducers. In addition, precise control of the inducer concentration on the treatment spot is difficult.

Thus, use of an inducer is a large problem in practical application of environmental remediation treatment utilizing microorganisms.

In order to solve the problem, Nelson et al. developed a method using tryptophan as an inducer for degradation of volatile organic chlorinated compounds (Japanese Patent Application Laid-Open No. 4-502277). Tryptophan, however, is a very expensive substance, and although tryptophane has no toxicity or risk as a substance, it is not preferable to introduce excessive carbon and nitrogen sources into environment since it may induce eutrophication. In addition, the problem that tryptophan serves as a competitive inhibitor in degradation of TCE still remains.

Shields et al. obtained a mutant strain of *Pseudomonas cepacia* G4 (changed to *Pseudomonas* sp. upon deposition to ATCC) by the transposon technique, which mutant strain does not require an inducer (in this case, phenol or toluene) and can degrade TCE (Appl. Environ. Microbiol., 58, 3977 (1992), International Publication No. WO/19738). Also, a mutant not requiring methane as the inducer has been isolated from *Methylosinus trichosporium* OB3b, a methanotroph capable of degrading TCE (U.S. Pat. No. 5,316, 940).

Japanese Patent Application Laid-Open No. 8-294387 also discloses strain JM1 (FERM BP-5352) capable of degrading volatile organic chlorinated compounds and aromatic compounds without requiring an inducer, isolated by nitrosoguanidine mutagenization of strain J1 (FERM BP-5102). While, it has been studied to introduce resting cells expressing TCE-degrading activity into the remediation site after the preculture of the cells in the presence of an inducer (Environ. Sci. Technol., 30, 1982 (1996)).

It has been reported that remediation treatment not requiring the inducer actually makes the remediation treatment easy and efficient compared to the conventional treatment using inducers.

However, the growth control of the degrading microorganisms is very important for both the expression of the degradation activity on demand and the continuation of degradation. When resting cells are used, it is a problem to be solved that TCE cannot be degraded beyond the amount and period of degradation capacity of the introduced resting cells. In addition, in a large scale treatment, there are further problems that degradation activity will decrease since it takes a long time to prepare resting cells; the treating apparatus must be large in scale; treatment process is complicated; and the cost may be unfavorably high. Accordingly, it has been attempted to introduce a plasmid carrying a DNA fragment containing a gene region encoding oxygenase or hydroxylase into a host microorganism to make the host express the TCE degradation activity constitutively or inducibly using a harmless inducer. For example, there are *Pseudomonas mendocina* KR-1 (Japanese Patent Application Laid-Open No. 2-503866, *Pseudomonas putida* KWI-9 (Japanese Patent Application Laid-Open No. 6-105691), *Pseudomonas putida* BH (Summary of 3rd Conference on Pollution of Ground Water/Soil and Its Protective Countermeasure, p.213 (1994)), and a transformant carrying both a toluene degradation enzyme gene derived from *Pseudomonas putida* F1 and a biphenyl degradation enzyme gene derived from *Pseudomonas pseudoalkaligenes* (Japanese Patent Application Laid-Open No. 7-143882).

However, the reported TCE degradation activity of the transformants are low, and the advantages of the transformants has not been fully utilized for efficient degradation of TCE, such as the ease of degradation control, freedom in designing recombinant, an d no requirements for inducers.

SUMMARY OF THE INVENTION

It is an object of the present invention to provide a novel DNA fragment encoding a toluene monooxygenase of a high efficiency in degrading aromatic compounds and/or organic chorine compounds, a novel recombinant DNA containing the DNA fragment, and a transformant containing the recombinant DNA. It is another object of the present invention to provide an efficient biodegradation method for volatile organic chlorinated compounds such as trichloroethylene (TCE) and dichloroethylene (DCE) and aromatic compounds such as toluene, benzene, phenol, and cresol using the transformant, specifically an efficient environmental remediation method useful for purifying aqueous media such as wastewater and effluent containing chlorinated aliphatic hydrocarbon compounds or aromatic compounds, remedying soil polluted with chlorinated aliphatic hydrocarbon compounds or aromatic compounds, and purifying air (gas phase) polluted with chlorinated aliphatic hydrocarbon compounds.

To achieve the above objects, the inventors of the resent invention strained to isolate the gene encoding toluene monooxygenase from *Burkholderia cepacia* KK01 (previously *Pseudomonas cepacia*, deposited in the National Institute of Bioscience and Human Technology, Agency of Industrial Science and Technology in accordance with the requirements of the Budapest Treaty, Deposit Date: Mar. 11, 1992, Accession No. FERM BP-4235) having a toluene monooxygenase that oxidizes toluene to ortho-cresol and 3-methylcatechol. Successful isolation and characterization of the gene completed the present invention.

According to one aspect of the present invention, there is provided a DNA fragment of about 5.8 Kb containing a toluene monooxygenase gene having a following restriction map, where 1 BamHI restriction site, 2 EcoRI restriction sites, 1 HpaI restriction site, 1 KpnI restriction site, 1 NcoI restriction site, 1 NspV restriction site, 1 SacI restriction site, 2 SmaI restriction sites, 3 SphI restriction sites, 2 XhoI restriction sites, no ClaI restriction site, no DraI restriction site, no EcoRV restriction site, no HindIII restriction site, no NdeI restriction site, no NheI restriction site, no PvuII restriction site, no ScaI restriction site, no Sse8387I restriction site, no StuI restriction site, and no XbaI restriction site are resent.

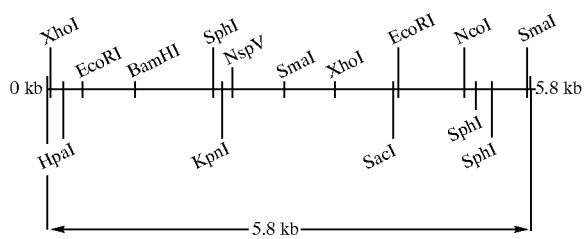

According to another embodiment of the present invention, there is provided a DNA fragment having the nucleotide sequence of SEQ ID NO: 1 with deletion, substitution and/or addition of one or more nucleotides, still encoding an active toluene monooxygenase.

Further, according to one aspect of the present invention, there is provided a recombinant DNA comprising a vector enabling maintenance or replication in a host and a DNA fragment of about 5.8 Kb containing a toluene monooxygenase gene having a following restriction map, where 1 BamHI restriction site, 2 EcoRI restriction sites, 1 HpaI restriction site, 1 KpnI restriction site, 1 NcoI restriction site, 1 NspV restriction site, 1 SacI restriction site, 2 SmaI restriction sites, 3 SphI restriction sites, 2 XhoI restriction sites, no ClaI restriction site, no DraI restriction site, no EcoRV restriction site, no HindIII restriction site, no NdeI restriction site, no NheI restriction site, no PvuII restriction site, no ScaI restriction site, no Sse8387I restriction site, no StuI restriction site, and no XbaI restriction site are present.

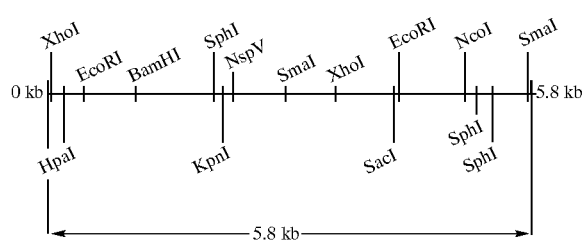

Further, according to another embodiment of the present invention, there is provided another recombinant DNA comprising a vector enabling maintenance or replication in a host, and a DNA fragment ligated thereto having the nucleotide sequence of SEQ ID No: 1 with deletion, substitution and/or addition of one or more bases, still encoding an active toluene monooxygenase.

According to still another aspect of the present invention, there is provided another recombinant DNA comprising a vector enabling maintenance or replication in a host, and a DNA fragment containing a region encoding a toluene monooxygenase, where the region comprises a first sequence encoding a polypeptide TomL having an amino acid sequence of SEQ ID NO: 3, a second sequence encoding a polypeptide TomM having an amino acid sequence of SEQ ID NO: 4, a third sequence encoding a polypeptide TomN having an amino acid sequence of SEQ ID NO: 5, a fourth sequence encoding a polypeptide TomO having an amino acid sequence of SEQ ID NO: 6, and a fifth sequence encoding a polypeptide TomP having an amino acid sequence of SEQ ID NO: 7, and the first to fifth sequences are aligned so that expressed TomL-TomP can form an active monooxygenase protein.

According to still another aspect of the present invention, there is provided another recombinant DNA comprising a vector enabling maintenance or replication in a host, and a DNA fragment containing a region encoding a toluene monooxygenase, where the region comprises a first sequence encoding a polypeptide TomL having an amino acid sequence of SEQ ID NO: 3, a second sequence encoding a polypeptide TomM having an amino acid sequence of SEQ ID NO: 4, a third sequence encoding a polypeptide TomN having an amino acid sequence of SEQ ID NO: 5, a fourth sequence encoding a polypeptide TomO having an amino acid sequence of SEQ ID NO: 6, and a fifth sequence encoding a polypeptide TomP having an amino acid sequence of SEQ ID NO: 7, and the first to fifth sequences are aligned so that expressed TomL-TomP can form an active monooxygenase protein, wherein one or more nucleotides have been deleted, substituted, or added in at least one of the sequences with the proviso that the activity of toluene monooxygenase is not impaired.

According to still another aspect of the present invention, there is provided a DNA fragment containing a region encoding a polypeptide TomK having an amino acid sequence of SEQ ID NO: 2 wherein the function of TomK is to enhance a toluene monooxygenase activity of a protein consisting at least of TomL to TomP, or encoding a variant TomK having an amino acid sequence varied from SEQ ID NO: 2 with the proviso that the function of TomK is not impaired.

According to still another aspect of the present invention, there is provided a recombinant DNA comprising a vector; a promoter; and a DNA fragment containing a region encoding a toluene monooxygenase, where the region comprises a first sequence encoding a polypeptide TomL having an amino acid sequence of SEQ ID NO: 3, a second sequence encoding a polypeptide TomM having an amino acid sequence of SEQ ID NO: 4, a third sequence encoding a polypeptide TomN having an amino acid sequence of SEQ ID NO: 5, a fourth sequence encoding a polypeptide TomO having an amino acid sequence of SEQ ID NO: 6, and a fifth sequence encoding a polypeptide TomP having an amino acid sequence of SEQ ID NO: 7, and the first to fifth sequences are aligned so that expressed TomL-TomP can form an active monooxygenase protein;
    wherein the promoter is linked to the DNA fragment in a manner allowing expression of the toluene monooxygenase protein encoded by the DNA fragment.

According to still another aspect of the present invention, there is provided a recombinant DNA comprising a vector; a promoter; and a DNA fragment containing a region encoding a toluene monooxygenase, where the region comprises a first sequence encoding a polypeptide TomL having an amino acid sequence of SEQ ID NO: 3, a second sequence encoding a polypeptide TomM having an amino acid sequence of SEQ ID NO: 4, a third sequence encoding a polypeptide TomN having an amino acid sequence of SEQ ID NO: 5, a fourth sequence encoding a polypeptide TomO having an amino acid sequence of SEQ ID NO: 6, and a fifth sequence encoding a polypeptide TomP having an amino acid sequence of SEQ ID NO: 7, and the first to fifth sequences are aligned so that expressed TomL-TomP can form an active monooxygenase protein,
    wherein one or more nucleotides have been deleted from, substituted in, and/or added to at least one of the sequences of the DNA fragment with the proviso that the protein does not loose toluene monooxygenase activity,
    wherein the promoter and the DNA fragment are functionally linked in a manner enabling expression of the toluene monooxygenase protein encoded by the DNA fragment.

According to still another aspect of the present invention, there is provided a recombinant DNA comprising a vector; a first promoter and a first DNA fragment functionally linked thereto; and a second promoter and a second DNA fragment functionally linked thereto; wherein the first DNA fragment contains a region encoding a polypeptide TomK having an amino acid sequence of SEQ ID NO: 2 wherein the function of TomK is to enhance a toluene monooxygenase activity of a protein consisting at least of TomL to TomP, or encoding a variant TomK having an amino acid sequence varied from SEQ ID NO: 2 with the proviso that the function of TomK is not impaired; the second DNA fragment contains a region encoding a toluene monooxygenase, where the region comprises a first sequence encoding a polypeptide TomL having an amino acid sequence of SEQ ID NO: 3, a second sequence encoding a polypeptide TomM having an amino acid sequence of SEQ ID NO: 4, a third sequence encoding a polypeptide TomN having an amino acid sequence of SEQ ID NO: 5, a fourth sequence encoding a polypeptide TomO having an amino acid sequence of SEQ ID NO: 6, and a fifth sequence encoding a polypeptide TomP having an amino acid sequence of SEQ ID NO: 7, and the first to fifth sequences are aligned so that expressed TomL-TomP can form an active monooxygenase protein, wherein one or more nucleotides have been deleted from, substituted in, and/or added to at least one of the sequences of the second DNA fragment with the proviso that the protein does not loose toluene monooxygenase activity,
    wherein the vector is linked to the DNA fragment in a manner enabling expression of the toluene monooxygenase protein encoded by the DNA fragment.

Further, according to still another aspect of the present invention, there is provided a transformant obtainable by introducing a recombinant DNA comprising a vector enabling maintenance or replication in a host and a DNA fragment of about 5.8 Kb containing a toluene monooxygenase gene having a following restriction map, where 1 BamHI restriction site, 2 EcoRI restriction sites, 1 HpaI restriction site, 1 KpnI restriction site, 1 NcoI restriction site, 1 NspV restriction site, 1 SacI restriction site, 2 SmaI restriction sites, 3 SphI restriction sites, 2 XhoI restriction sites, no ClaI restriction site, no DraI restriction site, no EcORV restriction site, no HindIII restriction site, no NdeI restriction site, no NheI restriction site, no PvuII restriction site, no ScaI restriction site, no Sse83871 restriction site, no StuI restriction site, and no XbaI restriction site are present.

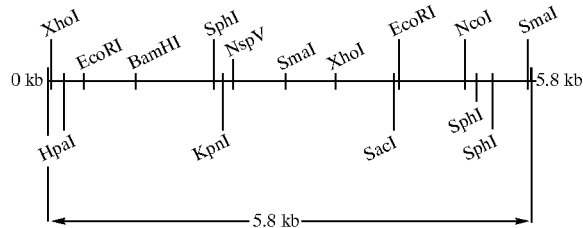

Further, according to still another aspect of the present invention there is provided a transformant obtainable by introducing a recombinant DNA into a host microorganism, where the recombinant DNA comprises a vector enabling maintenance or replication in a host, and a DNA fragment ligated thereto having the nucleotide sequence of SEQ ID NO: 1 with deletion, substitution and/or addition of one or more bases, still encoding an active toluene monooxygenase.

Further, according to still another aspect of the present invention, there is provided a transformant obtainable by introducing a recombinant DNA comprising a vector, a promoter and a DNA fragment into a host microorganism where the DNA fragment contains a region encoding a toluene monooxygenase, where the region comprises a first sequence encoding a polypeptide TomL having an amino acid sequence of SEQ ID NO: 3, a second sequence encoding a polypeptide TomM having an amino acid sequence of SEQ ID NO: 4, a third sequence encoding a polypeptide TomN having an amino acid sequence of SEQ ID NO: 5, a fourth sequence encoding a polypeptide TomO having an amino acid sequence of SEQ ID NO: 6, and a fifth sequence encoding a polypeptide TomP having an amino acid sequence of SEQ ID NO: 7, and the first to fifth sequences are aligned so that expressed Tom L-TomP can form an active monooxygenase protein;
wherein the promoter and the DNA fragment are functionally linked in a manner enabling expression of the toluene monooxygenase protein encoded by the DNA fragment.

According to still another aspect of the present invention, there is provided a method for producing a toluene monooxygenase, which comprises a step of making the transformant according to any one of the embodiment of the present invention mentioned above to produce the toluene monooxygenase being a gene product of the recombinant DNA introduced in the transformant.

According to still another aspect of the present invention, there is provided a method for degrading at least either of a chlorinated aliphatic hydrocarbon compound or an aromatic compound, which comprises a step of degrading at least either of the chlorinated aliphatic hydrocarbon compound or aromatic compound using the transformant according to any one of the aspects of the present invention mentioned above.

According to still another aspect of the present invention, there is provided a method for cleaning a medium contaminated with at least either of a chlorinated aliphatic hydrocarbon compound or an aromatic compound, which comprises a step of degrading at least either of a chlorinated aliphatic hydrocarbon compound or an aromatic compound using the transformants according to any one of the aspects of the present invention mentioned above.

According to still another aspect of the present invention, there is provided a method of remedying an environment polluted with at least either of a chlorinated aliphatic hydrocarbon compound or an aromatic compound as a pollutant, comprising a step of degrading the pollutants using the transformant according to any one of the aspects of the present invention mentioned above.

According to still another aspect of the present invention, there is provided a component polypeptide having any one of amino acid sequences of SEQ ID Nos: 2–8, which can constitute a toluene monooxygenase.

According to still another aspect of the present invention, there is provided a toluene monooxygenase comprising at least component polypeptides TomL-TomP of amino acid sequences of SEQ ID NOs: 3–7.

According to still another aspect of the present invention, there is provided a variant toluene monooxygenase comprising at least component polypeptides TomL-TomP of amino acid sequences of SEQ ID Nos.: 3–7 wherein one or more amino acids have been deleted from, substituted to, and/or added to the polypeptides with the proviso that the toluene monooxygenase does not loose its activity.

DETAILED DESCRIPTION OF THE PREFERRED EMBODIMENTS

Figure 1:
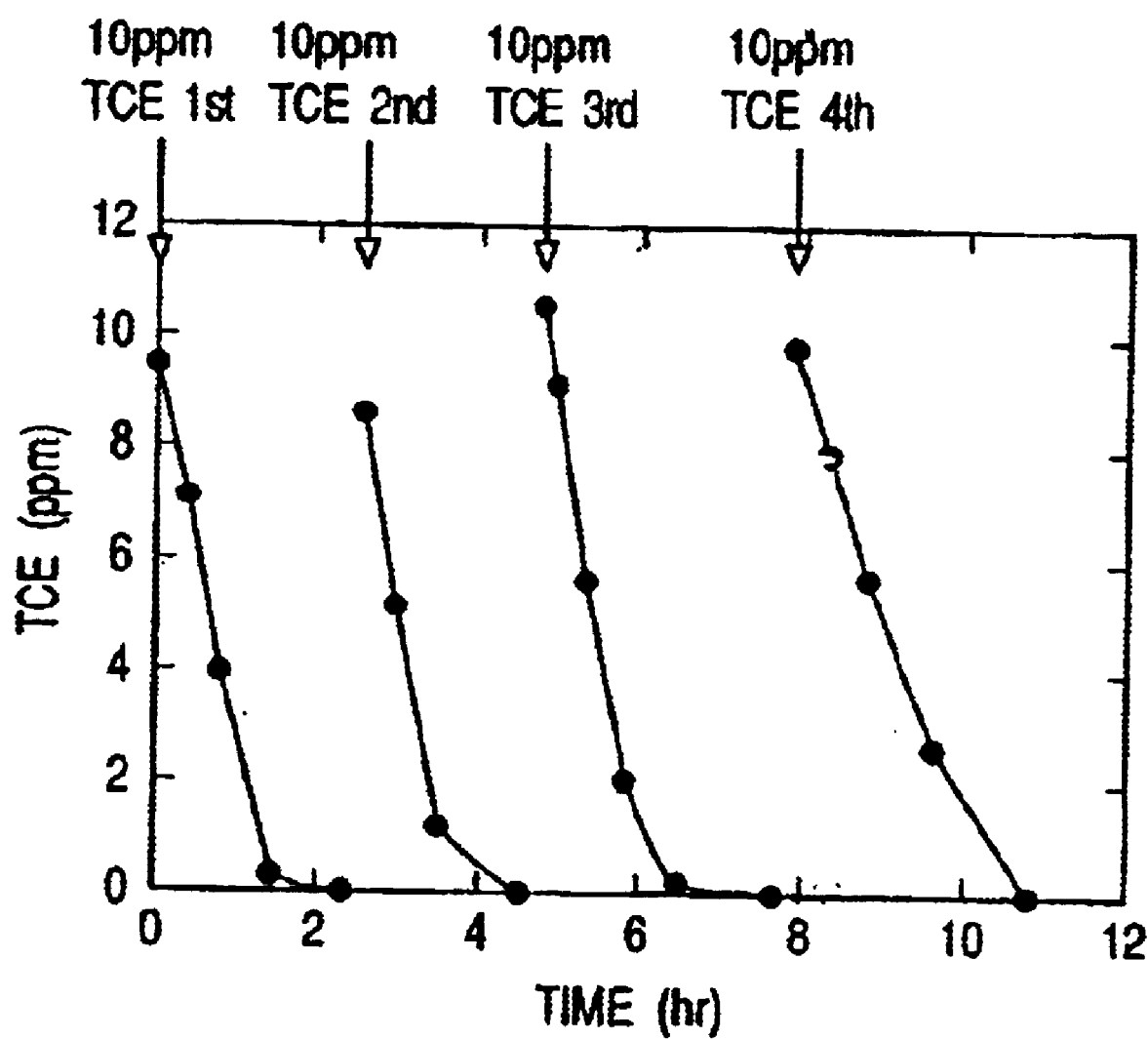
FIG. 1 shows time-course changes in TCE in the gas phase in Example 3.

The DNA fragment containing a toluene monooxygenase gene according to the present invention is isolated from *Burkholderia cepacia* strain KK01 (FERM BP-4235, hereinafter referred to as Strain KK01). The microbiological characteristics and culture conditions of Strain KK01 are as follows (see Japanese Patent Application Laid-Open No. 6-22769).

Strain KK01
  Morphological Characteristics
  (1) Gram staining: Negative
  (2) Size and shape: Rod of 1.0–2.0 µm in length and 0.5 µm in width
  (3) Motility: Motile
B. Growth on Various Culture Media

| Medium | Growth temperature (° C.) | Growth |
|---|---|---|
| Blood agar medium | 37 | + |
| Lactose agar medium | 37 | + |
| Chocolate agar medium | 37 | ++ |
| GMA | 37 | − |
| Scylo | 37 | − |
| Standard agar medium | 4 | − |
| Standard agar medium | 25 | ± |
| Standard agar medium | 37 | + |
| Standard agar medium | 41 | ± |

C. Physiological Characteristics
(1) Aerobic or anaerobic: obligate aerobic
(2) Sugar degradation mode: Oxidation (3) Oxidase production: +
(4) Silver nitrate reduction: +
(5) Hydrogen sulfide production: −
(6) Indole production: −
(7) Urease production: −
(8) Gelatin liquefaction: −
(9) Arginine hydrolysis: −
(10) Lysine decarboxylation: +
(11) Ornithine decarboxylation: −
(12) Utilization of citric acid: +
(13) Methyl carbinol acetyl reaction (VP reaction): −
(14) Detection of tryptophan deaminase:
(15) ONPG:
(16) Assimilation of carbohydrates Glucose: +

Fructose: +

Maltose: +

Galactose: +

Xylose: +

Mannitol: ±

Sucrose: −

Lactose: +

Esculin: −

Inositol: −

Sorbitol: −

Rhamnose: −

Melibiose: −

Amygdalin: −

L-(+)-arabinose: +

Isolation of the DNA fragment according to the present invention is achieved by partial digestion of the total DNA of strain KK01 with a restriction enzyme Sau3AI. Specifically, total DNA can be prepared by the standard method, in which the above microorganism is grown in a suitable medium, for example, LB medium (containing 10 g of trypton, 5 g of yeast extract, and 5 g of sodium chloride in 1 litter) and then cells are disrupted, for example, in the presence of sodium dodecyl sulfate (SDS) at 70° C. The total DNA is then partially digested by Sau3AI to obtain a DNA fragment of about 5.8 Kb carrying a toluene monooxygenase gene. The DNA fragment thus obtained is ligated to a plasmid vector completely digested by BamHI, for example, pUC18, and the recombinant vector is introduced into competent cells of, for example, E. coli JM109, prepared by the Hanahan method to obtain transformants. Then, transformants can be selected by a suitable method, for example, by culturing cells on an LB medium plate containing ampicillin.

In order to select a transformant containing a recombinant vector carrying a toluene monooxygenase gene from the above transformants, it is preferable to add cresol, phenol, or the like to LB medium for transformant selection in advance. The transformant carrying a toluene monooxygenase gene can be selected as brown colonies, since these substrates are monooxygenated by toluene monooxygenase to produce methylcatechol or catechol-which is then autoxidized to develop color. Alternatively, after culturing cells on an ordinary LB medium plate, various substrates may be sprayed onto the plate to select brown colonies in a similar manner.

The isolated DNA fragment of about 5.8 Kb has the following restriction sites:

| Restriction enzyme | Number of restriction sites |
|---|---|
| BamHI | 1 |
| EcoRI | 2 |
| HpaI | 1 |
| KpnI | 1 |
| NcoI | 1 |
| NspV | 1 |
| SacI | 1 |
| SmaI | 2 |
| SphI | 3 |
| XhoI | 2 |

The DNA fragment has no ClaI, DraI, EcoRV, HindIII, NdeI, NheI, PvuII, ScaI, Sse83871, StuI, or XbaI restriction site.

The restriction map of the DNA fragment of the present invention is as shown above. Toluene monooxygenase genes derived from Burkholderia cepacia G4 5223 PR1 (U.S. Pat. No. 5,543,317), derived from Burkholderia sp. JS150 (Appl. Environ. Microbiol., 61, 3336 (1995), derived from Pseudomonas pickettii PKO1 (J. Bacteriol., 176, 3749 (1994)), and derived from Pseudomonas mendocina KR1 (J. Bacteriol., 173, 3010 (1991)) were reported. Phenol hydroxylases reported to have a similar structure are derived from Acinetobacter calcoaceticus NCIIB8250 (Mol. Microbiol., 18, 13 (1995)), Pseudomonas sp. CF600 (J. Bacteriol., 172, 6826 (1990)), Pseudomonas spp. (J. Bacteriol., 177, 1485 (1995)), and Pseudomonas putida P35X (Gene, 151, 29 (1994)). The DNA fragment of the present invention has, however, a restriction map different from any of those. It is thus clear that the DNA fragment of the present invention contains a novel toluene monooxygenase gene.

Although the DNA fragment thus obtained can sufficiently enables the degradation of aromatic compounds and/or chlorinated aliphatic hydrocarbon compounds even in pUC18, it can be integrated in an expression vector or a vector of a wide host range to improve the degradation ability or to be optimized for the treatment site.

The plasmid according to the present invention can be constructed from following elements:

1) Toluene monooxygenase gene;
2) Marker gene (drug-resistance, auxotrophic complement, or the like); and
3) Vector containing an autonomous replication sequence (plasmid, or the like).

As the toluene monooxygenase gene, the DNA fragment of about 5.8 kb as shown above can be employed by itself, or a constitution containing elements necessary for a toluene monooxygenase activity can be also employed, for example, with or without spacer sequences. Further, each element can be varied with the proviso that its function is not impaired. These variations can be attained by changing DNA sequences encoding them.

As the drug-resistance genes, an ampicillin resistance gene, a kanamycin (G418, neomycin) resistance gene, a tetracycline resistance gene, a chloramphenicol resistance gene, a hygromycin resistance gene can be employed. For auxotrophic complement, a gene sequence to supply the nutrient required by the host organism is used. Typically, a gene enabling the synthesis of the required amino acid is utilized.

As the autonomous replication sequences, a sequence derived from plasmid RSF1010, which can function as a wide host range replication region in most of the gram-negative bacteria, can be employed. It can be also employed vector pBBR122 (Mo Bi Tec) containing a wide host range replication region which does not belong to any incompatible groups, IncP, IncQ, or IncW or the like.

For the recombinant plasmid according to the present invention, various promoters and terminators can be employed and various factors can be further introduced to improve and control the ability of degrading aromatic compounds and/or chlorinated aliphatic hydrocarbon compounds. Specifically, promoters such as lac, trc, tac, T3, and T7 can be employed. As a terminator, a rrnB operon terminator or the like can be employed. Also, introduction of a repressor gene such as lacIq and a lac operator enables expression control with an inducer such as isopropyl thiogalactoside (IPTG). Alternatively, the absence of these suppressor and operator as elements, enables constitutive expression of degradation activity. In addition, a temperature-sensitive control system or the like can be employed.

For recombination of a DNA fragment containing the toluene monooxygenase gene into an expression vector containing these regulating elements, natural restriction sites can be utilized as it is, or restriction sites may be newly created by site-directed mutagenesis or a polymerase chain reaction using a primer involving base substitution. In general, recombination into an expression vector often utilizes NcoI restriction sites. It is convenient to design so as to create an NcoI restriction site in the initiation codon ATG or GTG region by site-directed mutagenesis or primer design. Known methods using an adaptor can be employed. For optimization of expression, the DNA fragment may be properly deleted using exonuclease III or Ba131 nuclease. As described above, molecular biological techniques suitable for the purpose can be employed for recombination into an expression vector.

As a method for introducing the recombinant plasmid carrying a desired gene into a host organism, any methods that can introduce a foreign gene into a host can be employed, and known methods, for example, the calcium chloride method, the electroporation method, and the conjugation transfer method can be employed.

In the present invention, any microorganisms can be used as a host organism so long as it can express the aromatic compounds and/or chlorinated aliphatic hydrocarbon compounds-degrading activity after the introduction of the recombinant plasmid, including the genera *Escherichia, Pseudomonas, Burkholderia, Acinetobacter, Moraxella. Alcaligenes, Vibrio, Nocardia, Bacillus, Lactobacillus, Achromobacter, Arthrobacter, Micrococcus, Mycobacterium, Methylosinus, Methylomonas, Welchia, Methylocystis, Nitrosomonas, Saccharomyces, Candida, Torulopsis,* and *Ralstonia*.

In addition, the aromatic compounds and/or chlorinated aliphatic hydrocarbon compounds-degrading microorganisms such as strain J1, strain JM1, *Pseudomonas* sp. strain TL1, strain KK01, *Pseudomonas alcaligenes* strain KB2, *Alcaligenes* sp. strain TL2, and *Vibrio* sp. strain KB1 can be employed as a host. These strains have been deposited in the National Institute of Bioscience and Human Technology, Agency of Industrial Science and Technology of Japan. The date of deposit, Accession No., and microbiological characteristics of these strains other than the strain KK01 already described are shown below.

Strain J1 (Deposit date: May 25, 1994, Accession No. FERM BP-5102)
A. Morphological characteristics
  Gram staining: Positive
  Size and shape of cells: Polymorphous rod of 1–6 $\mu$m in length and about 0.5–2 $\mu$m in width
  Mobility: Negative
  Colony: Cream to light pink, sticky
B. Growth on various media
  BHIA: Good growth
  MacConkey: No growth
C. Optimal temperature for growth: 25° C.>30° C.>35° C.
D. Physiological characteristics
  Aerobic or anaerobic: aerobic
  TSI (slant/butt): Alkaline/alkaline, $H_2S$ (−)
  Oxidase: Negative
  Catalase: Positive
  Sugar fermentation
    Glucose: Negative
    Sucrose: Negative
    Raffinose: Negative
    Galactose: Negative
    Maltose: Negative
  Urease: Positive
  Esculin: Positive
  Nitric acid: Negative Strain JM1 (Deposit date: Jan. 10, 1995, Accession No. FERM BP-5352)
  Gram staining and morphology: Gram-negative rod
  Growth on various media
    BHIA: Good growth
    MacConkey: Possible to grow
  Colony color: Cream
  Optimal temperature for growth: 25° C.>30° C.>35° C.
  Mobility: Negative (semi-fluid medium)
  TSI (slant/butt): Alkaline/alkaline, $H_2S$ (−)
  Oxidase: Positive (weak)
  Catalase: Positive
  Sugar fermentation
    Glucose: Negative
    Sucrose: Negative
    Raffinose: Negative
    Galactose: Negative
    Maltose: Negative
  Urease: Positive
  Esculin hydrolysis ($\beta$-glucosidase): Positive
  Nitrate reduction: Negative
  Indole production: Negative
  Glucose acidification: Negative
  Arginine dehydrase: Negative
  Gelatin hydrolysis (protease): Negative
  $\beta$-Galactosidase: Negative
  Assimilation of compounds
    Glucose: Negative
    L-Arabinose: Negative
    D-Mannose: Negative
    D-Mannitol: Negative
    N-Acetyl-D-glucosamine: Negative
    Maltose: Negative
    Potassium gluconate: Negative
    n-Capric acid: Positive Adipic acid: Negative
dl-Malic acid: Positive
Sodium citrate: Positive
Phenyl acetate: Negative Strain J1 is an aromatic compound-assimilating bacterium which degrades organic chlorinated compounds with the participation of oxygenase. In spite of its excellent ability of degrading organic chlorinated compounds that it can almost completely degrade about 20 ppm of TCE at a low temperature of 15° C. close to natural environment such as soil, it requires aromatic compounds such as phenol, toluene, and cresol as a degradation inducer. Strain JM1 has the same microbiological characteristics as the parental strain J1 except that it can degrade organic chlorinated compounds in the absence of aromatic compounds such as phenol, toluene, and cresol as a degradation inducer.

Strain TL1 (Deposit date: Jan. 10, 1995, Deposit No. FERM P-14726/FERM BP-6923.
A. Gram staining and morphology: Gram-negative rod
B. Growth on various media
   Standard agar: Good growth
   MacConkey agar: Poor growth
C. Optimal temperature for growth: 25° C.>35° C.
D. Physiological characteristics
   Aerobic/anaerobic: Aerobic
   TSI (slant/butt): Alkaline/alkaline, $H_2S$ (−)
   Oxidase: Positive
   Catalase: Positive
   Oxidation/fermentation test: −/−
   Potassium nitrate reduction: Negative
   Indole production from L-tryptophan: Negative
   Glucose acidification: Negative
   Arginine dehydrase: Negative
   Urease: Negative
   Esculin hydrolysis (β-glucosidase): Negative
   Gelatin hydrolysis (protease): Negative
   β-Galactosidase: Negative
   Cytochrome oxidase: Positive
E. Assimilation of sugars, organic acids, etc.
   Glucose: Positive
   Arabinose: Positive
   D-Mannose: Negative
   D-Mannitol: Positive
   N-Acetyl-D-glucosamine: Negative
   Maltose: Negative
   Potassium gluconate: Positive
   n-Capric acid: Negative
   Adipic acid: Positive
   dl-Malic acid: Negative
   Sodium citrate: Negative
   Phenyl acetate: Negative Strain TL2 (Deposit date on Nov. 15, 1994, Deposit No. FERM P-14642/FERM BP-6913.
A. Gram staining and morphology: Gram-negative rod
B. Growth on various media
   Standard agar: Good growth
   MacConkey agar: Poor growth
C. Optimal temperature for growth: 25° C.>35° C.
D. Physiological characteristics
   Aerobic/anaerobic: Aerobic
   TSI (slant/butt): Alkaline/alkaline, $H_2S$ (−)
   Oxidase: Positive
   Catalase: Positive
   Oxidation/fermentation test: −/−
   Potassium nitrate reduction: Positive
   Indole production from L-tryptophan: Negative
   Glucose acidification: Negative
   Arginine dehydrase: Negative
   Urease: Negative
   Esculin hydrolysis (β-glucosidase): Negative
   Gelatin hydrolysis (protease): Negative
   β-Galactosidase: Negative
   Cytochrome oxidase: Positive
E. Assimilation of sugars, organic acids, etc.
   Glucose: Negative
   L-Arabinose: Negative
   D-Mannose: Negative
   D-Mannitol: Negative
   N-Acetyl-D-glucosamine: Negative
   Maltose: Negative
   Potassium gluconate: Positive
   n-Capric acid: Positive
   Adipic acid: Positive
   dl-Malic acid: Positive
   Sodium citrate: Positive
   Phenyl acetate: Positive Strain KB1 (Deposit date: Nov. 15, 1994, Deposit No. FERM P-14643/FERM BP-6914.
A. Gram staining and morphology: Gram-negative *bacillus*
B. Growth conditions on various media
   Standard agar: Good growth
   MacConkey agar: Good growth
C. Optimal temperature for growth: 25° C.>35° C.
D. Physiological characteristics
   Aerobic/anaerobic: Aerobic
   TSI (slant/butt): Alkaline/alkaline, H2 S(−)
   Catalase: Positive
   Oxidation/fermentation test: −/−
   Potassium nitrate reduction: Positive
   Indole productivity from L-tryptophan: Negative
   Glucose acidification: Negative
   Arginine dehydrase: Positive
   Urease: Positive
   Esculin hydrolysis (β-glucosidase): Negative
   Gelatin hydrolysis (protease): Negative
   β-Galactosidase: Negative
   Cytochrome oxidase: Positive
E. Assimilation of sugars, organic acids, etc.
   Glucose: Negative
   L-Arabinose: Negative
   D-Mannose: Negative
   D-Mannitol: Negative
   N-Acetyl-D-glucosamine: Positive
   Maltose: Negative
   Potassium gluconate: Positive
   n-Capric acid: Positive
   Adipic acid: Positive
   dl-Malic acid: Positive
   Sodium citrate: Negative Phenyl acetate: Positive Strain KB2 (Deposit date: Nov. 15, 1994, Accession No. FERM BP-5354)

A. Gram staining and morphology: Gram-negative rod
B. Growth on various media
   Standard agar: Good growth
   MacConkey agar: Good growth
C. Optimal temperature for growth: 25° C.>35° C.
   Growth at 42° C.: Good
D. Physiological characteristics
   Aerobic/anaerobic: Aerobic
   TSI (slant/butt): Alkaline/alkaline, $H_2S$ (−)
   Catalase: Positive
   Oxidation/fermentation test: −/−
   Potassium nitrate reduction: Positive
   Indole production from L-tryptophan: Negative
   Glucose acidification: Negative
   Arginine dehydrase: Negative
   Urease: Negative
   Esculin hydrolysis (β-glucosidase): Negative
   Gelatin hydrolysis (protease): Negative
   β-Galactosidase: Negative
   Cytochrome oxidase: Positive
E. Assimilation of sugars, organic acids, etc.
   Glucose: Negative
   L-Arabinose: Negative
   D-Mannose: Negative
   D-Mannitol: Negative
   N-Acetyl-D-glucosamine: Negative
   Maltose: Negative
   Potassium gluconate: Positive
   n-Capric acid: Negative
   Adipic acid: Positive
   dl-Malic acid: Positive
   Sodium citrate: Negative
   Phenyl acetate: Negative Further, in order to exploit the microbial degrading ability more effectively, it is preferable to select the host microorganism for recombinants from the microorganisms isolated to the environment to be treated, more preferably a dominant microorganism in the environment, considering environmental adaptation of the recombinant. Generally, in the natural world, microorganisms that have existed in an environment will adapt to the environment most probably, and the probability of the survival of foreign microorganisms introduced into the environment is not high. On the other hand, when a very strong microorganism is introduced from outside, it may disturb the existing ecosystem. Thus, the use of the indigenous microorganisms as a host is a superior method in environmental adaptability, survival, and safety.

A transformant to which a recombinant plasmid has been introduced may be cultured in the conditions suitable for the growth of the host. For example, a carbon and nitrogen source such as yeast extract, trypton, and peptone, and a inorganic salt such as sodium chloride and potassium chloride can be used. An M9 medium (containing 6.2 g of $Na_2HPO_4$, 3.0 g of $KH_2PO_4$, 0.5 g of NaCl, and 1.0 g of $NH_4Cl$ in 1 litter) supplemented with various minerals and suitable carbon sources such as sodium malate, sodium succinate, sodium lactate, sodium pyruvate, sodium glutamate, sodium citrate, etc. can also be employed. Further, yeast extract, trypton, peptone, etc. can be used in combination. The pH of the growth medium and culture temperature can be adjusted to those suitable for the host microorganism, although pH of about 5–9 and culture temperature of 15–37° C. are generally preferable.

A transformant containing a recombinant DNA carrying a toluene monooxygenase gene can be suitably employed for the treatment to degrade chlorinated aliphatic hydrocarbon compounds and aromatic compounds (hereinafter referred to as "pollution compounds") contained in a medium. In other words, the degradation treatment for the pollution compounds according to the present invention can be carried out by bringing the transformant into contact with the pollution compounds in an aqueous medium, soil, or a gas phase. Any method can be used to contact the degrading microorganisms with the pollution compounds so long as the microorganisms can express the degrading activity. Various methods such as a batch method, semi-continuous method, and continuous method can be employed. Microorganisms semi-immobilized or immobilized on an appropriate carrier can be also used. The subject such as polluted water, drainage, waste water, soil, and gas phase can be treated by various methods, as required. These treatment methods are described below.

The degradation treatment of the pollution compounds in an aqueous medium according to the present invention can be carried out by contacting the degrading microorganism with the pollution compounds in the aqueous medium. The representative treating methods are described below. However, the method according to the present invention is not limited thereto, but applicable for any clean-up of the pollution compounds in an aqueous medium.

The simplest method is, for example, to introduce the degrading microorganism directly into an aqueous medium contaminated with the pollution compounds. In this case, it is preferable to optimize the pH, salt concentrations, temperature, and pollutant concentrations of the aqueous medium according to the degrading microorganism.

As another application mode, the degrading microorganism is grown in a culture vessel, and an aqueous medium containing the pollution compounds is introduced into the vessel at a predetermined flow rate to degrade these compounds. The aqueous medium can be introduced and discharged continuously, intermittently or batch-wise according to the treatment capacity. It is preferable to optimize the system by a system control in accordance to the concentrations of the pollution compounds.

Alternatively, the degrading microorganism may be first attached to a carrier such as soil particles and the filled in a reactor vessel, to which an aqueous medium containing the pollution compounds is introduced for degradation treatment. In this case, any carrier can be employed not restricted to soil particles, but carriers having a high capacity to retain microorganisms and not preventing aeration are preferable. To provide the microorganism with habitats, it can be used various bioreactor carriers, for example, those conventionally employed in the pharmaceutical industry, food industry, and wastewater treatment systems. More specifically, there can be used inorganic particulate carries such as porous glass, ceramics, metal oxides, activated carbon, kaolinite, bentonite, zeolite, silica gel, alumina, and anthracite; gel carries such as starch, agar, chitin, chitosan, polyvinyl alcohol, alginic acid, polyacrylamide, carrageenan, and agarose; ion-exchange cellulose, ion-exchange resins, cellulose derivatives, glutaraldehyde, polyacrylic acid, polyurethane, polyester, or the like. As natural materials, cellulose materials such as cotton, hemp, and papers, and lignin materials such as saw dust and barks can be employed.

The degradation treatment of the pollution compounds in soil according to the present invention can be carried out by bringing the degrading microorganism in contact with the pollution compounds in the soil. The representative treating methods are described below. However, the method according to the present invention is not limited thereto but applicable to any clean-up of the pollution compounds in soil.

The simplest method is, for example, to introducing degrading microorganisms directly into the soil polluted with the pollution compounds. Introduction of the microorganism may be carried out by spraying it on the surface of the soil and, when the treatment extends to deep underground, by introducing it through the well arranged in the underground, wherein the application of pressure of air, water, etc. allows the microorganism to spread over the wide area of the soil and makes the process more effective. In this case, it is necessary to adjust various conditions of the soil so that they are suitable for the microorganism used for the process.

Another use is such that first the microorganism is attached to a carrier, next the carriers are charged into the reaction vessel, and then the reaction vessel is introduced into, primarily, the aquifer of the contaminated soil, to undergo degradation treatment.

The form of the reaction vessel is desirably like a fence or a film which can cover the wide area of the soil. Any carrier can be used, but it is preferable to use those having an excellent retention of microorganisms and not inhibiting aeration. As a material of the carrier, which can provide suitable habitats for microorganisms, for example, it can be used various bioreactor carriers, for example, those conventionally employed in the pharmaceutical industry, food industry, and wastewater treatment systems.

According to the present invention, the degradation treatment of the pollution compounds in gas phase can be achieved by contacting the microorganism with the contaminants in the gas phase. The representative modes are shown below, but are not intended to limit the present invention. The present invention is applicable to purification treatment of any gas phase contaminated with the pollution compounds.

One mode is, for example, such that the degradation microorganism is cultured in a culture vessel, and then the gas containing the pollution compounds is introduced into the vessel at a given flow rate to undergo degradation treatment. The method of introducing the gas is not limited specifically, but it is desirably such that introduction of the gas causes agitation of the culture medium and promote its aeration. Introduction and discharge of the gas may be carried out continuously, or it may be carried out intermittently according to the degradation capacity. A batch method is also applicable. Preferably such control is systematized in accordance with the concentrations of the pollution compounds to give optimum results.

Another mode is such that the microorganism is attached to a carrier like soil particles, next the carriers are put into a reaction vessel, and then the gas containing the pollution compounds is introduced into the vessel to undergo degradation treatment. Besides particles of soil, any carrier can be used, however, it is desirable to use those having an excellent retention of microorganisms and not inhibiting aeration. As a material of the carrier, which can provide suitable habitats for microorganisms, for example, it can be used various bioreactor carriers, for example, those conventionally employed in the pharmaceutical industry, food industry, and wastewater treatment systems.

As materials which can retain the degrading microorganism and supply it with nutrient, many examples can be found in the compost used in the agriculture, forestry and fisheries. Specifically, dry materials from plants, such as straw of grains, sawdust, rice bran, bean curd lees, bagasse and so on, and seafood wastes, such as shells of crabs and lobster and so on are applicable.

In purification of contaminated gas, the degrading microorganism may be introduced after the carrier material is packed. To make the degradation reaction efficient, it is preferable that the above-mentioned nutrient, water content, oxygen concentration, etc. are kept in desirable conditions. The ratio of the carrier to water in a reaction vessel may be determined considering the growth of the microorganism and aeration. The shape of the vessel may be selected considering the amount and concentration of the gas undergoing treatment, but preferably it is designed to enhance the contact of the gas with the microorganism held on the carrier. For example, column, tube, tank and box type are applicable. The vessel of these forms may be joined together with an exhaust duct and a filter to form one unit, or plural vessels may be connected according to the capacity.

Contaminated gas is sometimes adsorbed by the carrier material in the beginning of the reaction and there is very few case where the effect of utilizing microorganism may not be exhibit. After a certain period of time, however, it is thought that the contaminants adhered to the carrier material is degraded, and further contaminants can be adsorbed by the surface of the material to restore adsorption of the material. Thus, a constant decomposition rate is expected without saturation of the pollutant-eliminating ability.

The method according to the present invention is applicable for the treatment of waste liquid, soil and air in a closed system or open system. Moreover, microorganisms may be immobilized on a carrier, or various methods promoting their proliferation may be employed in combination.

The present invention is explained more specifically by means of the following examples.

EXAMPLE 1

Cloning of toluene monooxygenase gene of strain KK01

Cells of strain KK01 (FERM BP-4235) which can assimilate toluene were cultured in 100 ml of LB medium (containing 10 g of trypton, 5 g of yeast extract, and 5 g of sodium chloride in 1 liter) overnight, harvested and washed with 100 mM phosphate buffer (pH 8.0). To the cells thus obtained, 10 ml of STE (10 mM tris (pH 8.0)/1 mM EDTA/100 mM sodium chloride) and 1 ml of 10% sodium dodecyl sulfate (final concentration of about 1%) were added. After the cells were incubated at 70° C. for 30 minutes for lysis, phenol treatment and ethanol sedimentation were carried out. DNA thus obtained was dissolved in a 10 mM tris (pH 8.0)/1 mM EDTA buffer (TE).

The DNA thus obtained was dissolved at various concentrations and treated with a restriction enzyme Sau3AI (Takara Shuzo Co., Ltd.) at 37° C. for 15 minutes for partial digestion. Aliquots of the partial digestion products were applied to gel electrophoresis on 0.8% agarose gel to identify the samples almost digested to about 5–10 kb. These samples were applied to spin column HR-400 (Amarsham-Pharmacia) to purify DNA fragments.

The DNA fragments were ligated to plasmid pUC18 (Takara Shuzo Co., Ltd.) completely digested with a restriction enzyme BamHI (Takara Shuzo Co., Ltd.) and dephosphorylated with BAP (Takara Shuzo Co., Ltd.), using DNA Ligation Kit Ver. 2 (Takara Shuzo Co., Ltd.). Recombinant plasmids thus prepared were then introduced into the host *E. coli* HB101 (Takara Shuzo Co., Ltd.), and the cells were cultured on LB agar plates containing 100 μg/ml of ampicillin as a selection agent and 200 ppm phenol as an indicator for toluene monooxygenase activity. About 15,000 colonies of transformants grew on the plates.

Eight brown colonies were found in these colonies and picked up. Recombinant plasmid DNA carrying toluene monooxygenase gene was extracted from the cells of each brown colony and the restriction map thereof was determined. It was found that all recombinant plasmids derived from the 8 colonies had a common insertion fragment of 5.8 kb. A plasmid containing only the common fragment of 5.8 kb was designated as pKK01 and a restriction map of the inserted DNA fragment was made. A recombinant *E. coli* HB101 carrying a plasmid containing a 8.5 kb insertion fragment containing this common 5.8 kb fragment was deposited in the National Institute of Bioscience and Human Technology, Agency of Industrial Science and Technology in accordance with the Budapest Treaty under the accession No. FERM BP-6916. Its microbiological characteristics were identical to those of *E. coli* HB101 except that it can degrade aromatic compounds and chlorinated aliphatic hydrocarbon compounds.

In order to confirm that the inserted DNA fragment of pKK01 was derived from strain KK01, southern hybridization was performed. DNA was extracted from strain KK01 and completely digested with EcoRI (Takara Shuzo Co., Ltd.) or XhoI (Takara Shuzo Co., Ltd.), and then subjected to southern hybridization. The inserted DNA fragment of pKK01 was digested with BamHI-KpnI (Takara Shuzo Co., Ltd.) to obtain a DNA fragment of about 1.6 kb, and this was used as a probe. As a result, a strong signal was observed around 4.3 kb with the EcoRI-digested DNA, and around 4.2 kb with the XhoI digested DNA, in a good agreement with the lengths of the fragments predicted from the restriction map. Consequently, it was confirmed that the toluene monooxygenase gene contained in pKK01 was derived from the strain KK01.

EXAMPLE 2
Monooxygenation by *E. coli* HB101(pKK01)

The cells of *E. coli* HB101(pKK01) were inoculated in 100 ml of LB medium, cultured at 37° C. overnight, harvested, washed, and then resuspended in 100 ml of M9 medium (6.2 g of $Na_2HPO_4$, 3.0 g of $KH_2PO_4$, 0.5 g of NaCl, and 1.0 g of $NH_4Cl$ per liter) supplemented with a mineral stock solution of the following composition (3 ml/liter of M9 medium)(referred to as M9+mineral solution).
Composition of mineral stock solution

| | |
|---|---|
| Nitrilotriacetic acid | 1.5 g |
| $MgSO_4$ | 3.0 g |
| $CaCl_2$ | 0.1 g |
| $Na_2MoO_4$ | 0.1 g |
| $FeSO_4$ | 0.1 g |
| $MnSO_4$ | 0.5 g |
| NaCl | 1.0 g |
| $ZnSO_4$ | 0.1 g |
| $CuSO_4$ | 0.1 g |
| $AlK(SO_4)_2$ | 0.1 g |
| $H_3BO_3$ | 0.1 g |
| $NiCl_2$ | 0.1 g |

Distilled water (to 1,000 ml)

Then, 27.5 ml vials were prepared, and 10 ml aliquot of the above suspension was placed in each vial, which was then tightly sealed with a teflon-coated butyl rubber stopper and aluminum seal. Gaseous toluene or benzene was introduced into each vial with a syringe to a concentration of 100 ppm (a concentration supposing all toluene or benzene completely dissolved in the aqueous phase in the vial). After incubation at 30° C. for 3 hours, 1 ml aliquot was taken from each vial, and cells were removed by centrifugation and substances of 10,000 or higher in molecular weight were removed by ultrafiltration. Production of ortho-cresol and 3-methylcatechol from toluene and phenol and catechol from benzene was confirmed by HPLC, to show that toluene and benzene are monooxygenated by toluene monooxygenase encoded by the cloned DNA fragment.

EXAMPLE 3

Degradation of aromatic compounds and chlorinated aliphatic hydrocarbon compounds by *E. coli* HB101(pKK01)

The cells of *E. coli* HB101(pKK01) cultured as described in Example 2 were suspended in M9+mineral solution. Ten ml aliquots of the suspension were placed in 27.5 ml vials. Each vial was tightly sealed with a teflon-lined butyl rubber stopper and an aluminum seal. Gaseous trichloroethylene (TCE), cis-1,2-dichloroethylene (cis-1,2-DCE), trans-1,2-dichloroethylene (trans-1,2-DCE), 1,1-dichloroethylene (1,1-DCE), toluene, and benzene were injected into respective vials to a concentration of 5 ppm (a concentration supposing the introduced substance completely dissolved in the aqueous phase in the vial). The vials were shaken and incubated at 30° C. The concentrations of the respective compounds in the gas phase were measured by gas chromatography after 6 hours. The results are shown in Table 1. *E. coli* HB101 harboring pUC18 (*E. coli* HB101(pUC18)) was employed as a control and degradation was evaluated in the same manner.

Another experiment was carried out on TCE degradation in the same manner except that the initial TCE concentration was 10 ppm and when the TCE concentration in the gas phase reached about 0, the process was repeated for total three times. The results are shown in Table 2.

Similarly, phenol, ortho-cresol, meta-cresol and para-cresol were introduced into respective 27.5 ml vials each containing 10 ml of the cell suspension at a concentration of 50 ppm. Each vial was tightly sealed with a butyl rubber stopper and aluminum seal. The vials were shaken and incubated at 30° C. The quantities of the respective compounds in the liquid phase were determined by the amino antipyrine method with a spectrophotometer to obtain their concentrations after 6 hours. The results are shown in Table 2. *E. coli* HB101(pUC18) was employed as a control and degradation was evaluated in the same manner.

TABLE 1

| | *E.coli* HB101 (pKK01) | HB101 (pUC18) |
|---|---|---|
| TCE | 0 | 5.2 |
| cis-1,2-DCE | 0 | 4.9 |
| trans-1,2-DCE | 0 | 5.1 |
| 1,1-DCE | 0 | 5.3 |
| Toluene | 0 | 5.5 |
| Benzene | 0 | 4.9 |

(Unit: ppm)

TABLE 2

|  | E.coli HB101 (pKK01) | E.coli HB101 (pUC18) |
| --- | --- | --- |
| Phenol | 0 | 55 |
| Ortho-cresol | 0 | 49 |
| Meta-cresol | 0 | 47 |
| Para-cresol | 0 | 52 |

(Unit: ppm)

The above results show that E. coli HB101(pKK01) had an excellent ability to degrade aromatic compounds and chlorinated aliphatic hydrocarbon compounds.

EXAMPLE 4

Definition of toluene monooxygenase region

The toluene monooxygenase region was defined further by subcloning or stepwise deletion of plasmid pKK01 obtained in Example 1, using restriction sites thereof. Toluene monooxygenase activity was evaluated by the method in Example 3, and 5 ppm toluene was employed as a substrate.

First, a subclone pKK01 ABamHI in which a 0.7-kb fragment was deleted was prepared from PKK01 using the unique BamHI site at 0.7 kb. More specifically, pKK01 was completely digested by restriction enzymes BamHI and HindIII (Takara Shuzo Co., Ltd.) to obtain 2 fragments of 3.4 kb and 5.1 kb. The fragments were separated by agarose gel electrophoresis, and the 5.1 kb fragment was cut out and recovered from the gel and purified with a spin column HR-400 (Amarsham-Pharmacia). The fragment was ligated to pUCIB previously completely digested by BamHI and HindIII enzymes, and E. coli HB101 was transformed with the recombinant plasmids according to the conventional method. E. coli HB101 cells were then applied on an LB plate containing 100 µg/ml of ampicillin to select transformants. From the cells grown overnight in LB medium, plasmid DNA was extracted by an alkaline method to confirm the presence of pKK01 ΔBamHI, and a transformant carrying pKK01 ΔBamHI was isolated. E. coli HB101 (pKK01ΔBamHI) cells were evaluated for toluene monooxygenase activity. No degradation of toluene was observed, indicating that the 0.7-kb fragment is essential for toluene monooxygenase activity.

Then, a subclone pKK01ΔEcoRI was prepared by deleting a 0.3 kb fragment from pKK01 using the 0.3 kb EcoRI restriction site of pKK01. More specifically, pKK01 was partially digested by restriction enzyme EcoRI, and then self-ligated to transform E. coli HB101. The E. coli HB101 transformants were then selected on an LB plate containing 100 µg/ml of ampicillin. After the transformants were cultured in LB medium overnight, the plasmid DNA was extracted from the cells by the alkaline method to confirm the presence of pKK01ΔEcoR1 and a transformant carrying pKK01ΔEcoR1 was isolated. E, coli HB101 (pKK01ΔEcoR1) was evaluated for toluene monooxygenase activity. Degradation of toluene was observed, but the activity was lower than that of E. coli HB101(pKK01), indicating that the 0.3 kb fragment was not essential for toluene monooxygenase activity but necessary for full expression of the activity.

Further, the stepwise deletion method was employed to restrict the toluene monooxygenase region from the opposite direction. More specifically, stepwise deletion was introduced from the XbaI restriction site using XbaI (Takara Shuzo Co., Ltd.) restriction site and Sse8387I (Takara Shuzo Co., Ltd.) restriction site of pUC18. The step-wise deletion was carried out using Deletion Kit for Kilo-Sequence (Takara Shuzo Co., Ltd.) according to the experimental method described in the attached protocol. The results of the activity evaluation of various deletion clones thus obtained show that the region up to 4.9 kb is essential for expression of the activity and a region from 4.9 kb to 5.8 kb is not especially required for degradation activity.

EXAMPLE 5

Sequencing of Toluene Monooxygenase Gene

The nucleotide sequence of pKK01 was determined as follows. pKK01 was digested by various restriction enzymes and subcloned into pUC18 plasmid. Deletion clones were prepared from pKK01 or subclones of partial pKK01 using Deletion Kit for Kilo-Sequence (Takara Shuzo Co., Ltd.) to determine the nucleotide sequence of the 5.8-kb fragment encoding toluene monooxygenase by the dideoxy method. The dideoxy method was carried out using ABI PRISM Cycle Sequencing Kit (Perkin Elmer Corporation) according to the attached protocol for reaction conditions, etc. DNA recombination and Kilo-Sequence method were also performed according to the conventional methods or the manufacturer's protocols attached. The results of sequencing show that the DNA encoding toluene monooxygenase is contained in 5,828 bases comprised of 7 coding regions as shown by SEQ ID NO: 1; a region tomK encoding the amino acid sequence TomK of SEQ ID NO: 2; a region TomL encoding the amino acid sequence tomL of SEQ ID NO: 3; a region tomM S7 encoding an amino acid sequence TomM of SEQ ID NO: 4; a region tomN encoding an amino acid sequence TomN of SEQ ID NO: 5; a region tomO encoding an amino acid sequence (TomO) of SEQ ID NO: 6; a region tomP encoding an amino acid sequence TomP of SEQ ID NO: 7; and a region tomQ encoding an amino acid sequence TomQ of SEQ ID NO: 8.

Here, considering the results of Example 4 together, the polypeptide (TomK)(SEQ ID No: 2) encoded by tomK is not essential for expression of the activity but the presence of TomK clearly enhances the toluene monooxygenase activity. It is therefore desirable for sufficient expression of the activity that TomK is present as a component of toluene monooxygenase. The polypeptide (TomQ)(SEQ ID NO: 8) encoded by tomQ is not essential for expression of the activity. In addition, the toluene monooxygenase activity is not affected by the presence of TomQ. Thus, it is not essential to contain TomQ as a component of toluene monooxygenase.

In other words, any DNA fragment containing segments encoding the amino acid sequences of SEQ ID NOs: 3–7 as the components of toluene monooxygenase where these segments are aligned so that expressed TomL to TomP having the amino acid sequences of SEQ ID NOs: 3–7 can form a protein with a toluene monooxygenase activity is included in the preferred DNA fragment of the present invention. DNA fragments with variation in at least one segment of the DNA fragment with the proviso that the activity of toluene monooxygenase is not impaired are included in the preferred DNA fragments of the present invention.

DNA fragments further containing a region encoding the amino acid sequence TomK of SEQ ID NO: 2 or a variant in which the amino acid sequence of SEQ ID NO: 2 is changed with the proviso that it does not impair the property to enhance a toluene monooxygenase activity are also included in the preferred embodiment of the present invention.

It should be noted that, in tomK, a sequence corresponding to SD sequence is not found before the 1st ATG (216–218) but present before the 2nd ATG (234–236). Thus, in the following Sequence Listing, the polypeptide encoded by the nucleotide sequence beginning the base number 234 is designated as TomK.

In addition, in tomL, a sequence corresponding to SD sequence is not found before the 1st ATG (bases number 391–393) but present before GTG(463–465). Thus, in the following Sequence Listing, the polypeptide encoded by the nucleotide sequence beginning the base of number 463 is designated as SEQ ID: NO. 3 (TomL).

EXAMPLE 6
Recombination of Toluene Monooxygenase Gene into Expression Vectors

As expression vectors, pTrc99A (Amarsham-Pharmacia), pSE280 (Invitrogen), and pSE380 (Invitrogen) were employed. They contain an ampicillin-resistant gene as a marker, and pTrc99A has a sequence derived from pBR322, and pSE280 and pSE380 have those derived from ColEl as ori. All these 3 vectors contain a trc promoter and a rrnB terminator, and a ribosome-binding site is located before the NcoI restriction site. lacIq is contained in pTrc99A and pSE380 but not in pSE280.

To incorporate the toluene monooxygenase gene into these vectors, NcoI restriction sites were introduced in tomK and tomL. The following 5 primers (Takara Shuzo Co., Ltd.) were prepared to introduce the NcoI restriction site by PCR:

```
SEQ ID NO: 9  tom-K1 5'-AGTCCGCCATGGAGGCGACACCGATCATGAATCAGC-3'    36 mer

SEQ ID NO: 10 tom-K2 5-CACCGACCATGGATCAGCACCCCACCGATCTTTC-3'       34 mer

SEQ ID NO: 11 tom-L1 5'-TGCCGCCTTCCATGGGTTCTGCCGCGAACAGCAG-3'      34 mer

SEQ ID NO: 12 tom-L2 5'-AGCAAGCCATGGCCATCGAGCTGAAGACAGTCGACATCA-3' 39 mer

SEQ ID NO: 13 tail   5'-CCGACCATCACCTGCTCGGCCAGATGGAAGTCGAG-3'     35 mer
```

The tom-K1 was designed to introduce the NcoI restriction site at the 1st ATG region (bases 216–218 in the Sequence Listing) of tomK. Similarly, tom-K2 was designed to introduce the NcoI site at the 2nd ATG region (bases 234–236 in the SEQ ID NO: 1) of tomK; tomL-1 was designed to introduce the NcoI site at the 1st ATG region (bases 391–393 in SEQ ID NO: 1) of tomL; and tom-L2 was designed to introduce the NcoI site at the 1st GTG region (bases 463–465 in SEQ ID NO: 1) of tomL. Using primer combinations of the primer (5) with the respective primers (1)–(4) and the 8.5 kb fragment-containing plasmid DNA of FERM BP-6916 as the template, PCR was performed. PCR was carried out using Takara LA PCR Kit Ver. 2 (Takara Shuzo Co., Ltd.) with a reaction volume of 50 µl, repeating 30 times a cycle of reaction at 94° C. for 1 minute and 98° C. for 20 seconds followed by 72° C. for 5 minutes (shuttle PCR), then followed by reaction at 72° C. for 10 minutes. The reaction conditions were according to the manufacturer's protocol.

As a result, the combinations of the primers (1) and (5), (2) and (5), (3) and (5), and (4) and (5) gave the PCR products of about 5.6 kb, about 5.6 kb, about 5.4 kb, and about 5.4 kb, respectively. The respective DNA fragments were digested with the restriction enzyme NcoI (Takara Shuzo Co., Ltd.) to give the respective fragments of about 5.0 kb, about 5.0 kb, about 4.9 kb, and about 4.8 kb together with a fragment of about 0.6 kb. It shows that PCR products were completely digested by the restriction enzyme NcoI. These NcoI-digested products were purified using a spin column HR-4000 (Amarsham-Pharmacia) and used for the following ligation reaction.

The above expression vectors were completely digested with the restriction enzyme NcoI, dephosphorylated, subjected to phenol treatment, and purified with a spin column HR-400 (Amarsham-Pharmacia). The vectors were then ligated to the NcoI-digested PCR products to transform E. coli HB101 (Takara Shuzo Co., Ltd.) according to the conventional method. The transformed E. coli HB101 cells were then grown on LB plate containing 100 µg/ml of ampicillin for transformant selection. After the transformants were cultured in LB medium at 37° C. overnight, plasmid DNA was extracted by the alkaline method to examine the recombinant plasmids. Transformants in which the respective PCR fragments were accurately inserted into the NcoI restriction site of the respective expression vectors were obtained.

A list of the obtained recombinant plasmids are shown in Table 3.

TABLE 3

|  | tom-K1 | tom-K2 | tom-L1 | tom-L2 |
|---|---|---|---|---|
| pTrc99A | pK19 | pK29 | pL19 | pL29 |
| pSE280 | pK12 | pK22 | pL12 | pL22 |
| pSE380 | pK13 | pK23 | pL13 | pL23 |

EXAMPLE 7
Ability of E. coli HB101 Recombinant Strains to Degrade Aromatic Compounds and Chlorinated Aliphatic Hydrocarbon Compounds (without Induction with IPTG)

The cells of the E. coli strains, each harboring one of the 12 recombinant plasmids obtained as described in Example 6, were inoculated in 100 ml of LB medium, cultured at 37° C. overnight, harvested, washed, and suspended in an M9+mineral solution. Ten ml aliquots of the suspension were placed in 27.5 ml vials, and each vial was tightly sealed with a Teflon-coated butyl rubber stopper and aluminium seal. Then, gaseous trichloroethylene (TCE), cis-1,2-dichloroethylene (cis-1,2-DCE), trans-1,2-dichloroethylene (trans-1,2-DCE), 1,1-dichloroethylene (1,1-DCE), toluene, and benzene were added to respective vials with a syringe to a concentration of 20 ppm (supposing all of the introduced substance dissolved in the aqueous phase in the vial). The vials were shaken and incubated at 30° C. The concentrations of the respective compounds in the gas phase after 6 hour incubation were measured by gas chromatography. The results are shown in Table 4. E. coli HB101(pSE280) was employed as a control and degradation was evaluated in the same manner.

TABLE 4

|  | pK19 | pK29 | pL19 | pL29 | pK12 | pK22 | pL12 | pL22 |
|---|---|---|---|---|---|---|---|---|
| TCE | 4.5 | 5.2 | 7.8 | 7.5 | 0 | 0 | 0.4 | 0.2 |
| cis-1,2-DCE | 2.5 | 2.4 | 3.8 | 4.5 | 0 | 0 | 2.1 | 3.2 |
| trans-1,2-DCE | 3.1 | 4.2 | 5.2 | 5.8 | 0 | 0 | 1.5 | 1.4 |

TABLE 4-continued

| | | | | | | | | |
|---|---|---|---|---|---|---|---|---|
| 1,1-DCE | 7.2 | 6.6 | 8.9 | 9.1 | 0 | 0 | 1.2 | 0.9 |
| Toluene | 1.3 | 1.1 | 2.5 | 3.2 | 0 | 0 | 0 | 0 |
| Benzene | 4.8 | 5.1 | 7.3 | 6.8 | 0 | 0 | 0.9 | 0.5 |

| | pK13 | pK23 | pL13 | pL23 | pSE280 |
|---|---|---|---|---|---|
| TCE | 3.8 | 4.3 | 5.5 | 5.3 | 20.1 |
| cis-1,2-DCE | 0.9 | 0.7 | 1.5 | 1.8 | 18.9 |
| trans-1,2-DCE | 1.2 | 1.1 | 2.1 | 2.1 | 19.8 |
| 1,1-DCE | 2.5 | 2.4 | 5.1 | 4.9 | 20.7 |
| Toluene | 1.2 | 0.9 | 1.8 | 1.7 | 21.0 |
| Benzene | 3.5 | 3.3 | 4.8 | 4.4 | 20.2 |

(Unit: ppm)

Similarly, phenol, ortho-cresol, meta-cresol and para-cresol were introduced into respective 27.5 ml vials each containing 10 ml of the cell suspension at a concentration of 50 ppm. Each vial was tightly sealed with a butyl rubber stopper and aluminum seal. The vials were shaken and incubated at 30° C. The quantities of the respective compounds in the liquid phase were determined by the amino antipyrine method with a spectrophotometer to determine their concentrations after 6 hours. The results are shown in Table 5. *E. coli* HB101(pSE280) was employed as a control and degradation was evaluated in the same manner.

TABLE 5

| | pK19 | pK29 | pL19 | pL29 | pK12 | pK22 | pL12 | pL22 |
|---|---|---|---|---|---|---|---|---|
| Phenol | 0 | 0 | 0 | 0 | 0 | 0 | 0 | 0 |
| Ortho-cresol | 0 | 0 | 0 | 0 | 0 | 0 | 0 | 0 |
| Meta-cresol | 0 | 0 | 0 | 0 | 0 | 0 | 0 | 0 |
| Para-cresol | 0 | 0 | 0 | 0 | 0 | 0 | 0 | 0 |

| | pK13 | pK23 | pL13 | pL23 | pSE280 |
|---|---|---|---|---|---|
| Phenol | 0 | 0 | 0 | 0 | 50.6 |
| Ortho-cresol | 0 | 0 | 0 | 0 | 52.5 |
| Meta-cresol | 0 | 0 | 0 | 0 | 53.1 |
| Para-cresol | 0 | 0 | 0 | 0 | 50.5 |

(Unit: ppm)

The above results confirm that *E. coli* HB101 transformants harboring the expression vectors have an excellent ability to degrade the aromatic compounds and chlorinated aliphatic hydrocarbon compounds. It is shown that transformants harboring pTrc99A or pSE380-derived expression vectors express a lower degrading activity in a system not containing IPTG than those harboring pSE280-derived plasmids, since pSE280 lacks lacIg.

EXAMPLE 8

Ability of *E. coli* HB101 Transformants harboring Expression Vectors to Degrade Aromatic Compounds and Chlorinated Aliphatic Hydrocarbon Compounds (with Induction with IPTG)

Each *E. coli* HB101 transformant strain harboring one of the 12 recombinant plasmids obtained as described in Example 6, was inoculated in 100 ml of LB medium, cultured at 37° C. to reach $OD_{600}$ of about 0.8, and then IPTG was added to 1 mM concentration followed by further incubation at 37° C. for 5 hours. Then the cells were harvested, washed and suspended in an M9+mineral solution. Ten ml aliquots of the suspension were placed in 27.5 ml vials, and each vial was tightly sealed with a Teflon-coated butyl rubber stopper and aluminium seal. Then, gaseous trichloroethylene (TCE), cis-1,2-dichloroethylene (cis-1,2-DCE), trans-1,2-dichloroethylene (trans-1,2-DCE), 1,1-dichloroethylene (1,1-DCE), toluene, and benzene were added to respective vials with a syringe to a concentration of 20 ppm (supposing all of the introduced substance dissolved in the aqueous phase in the vial). The vials were shaken and incubated at 30° C. The concentrations of the respective compounds in the gas phase after 6 hour incubation were measured by gas chromatography. The results are shown in Table 6. *E. coli* HB101(pSE280) was employed as a control and degradation was evaluated in the same manner.

TABLE 6

| | pK19 | pK29 | pL19 | pL29 | pK12 | pK22 | pL12 | pL22 |
|---|---|---|---|---|---|---|---|---|
| TCE | 0 | 0 | 0 | 0 | 0 | 0 | 0.7 | 0.5 |
| cis-1,2-DCE | 0 | 0 | 0 | 0 | 0 | 0 | 1.9 | 2.1 |
| trans-1,2-DCE | 0 | 0 | 0 | 0 | 0 | 0 | 0.9 | 1.9 |
| 1,1-DCE | 0 | 0 | 0.7 | 0.5 | 0 | 0 | 0.8 | 0.7 |
| Toluene | 0 | 0 | 0 | 0 | 0 | 0 | 0 | 0 |
| Benzene | 0 | 0 | 1.2 | 2.1 | 0 | 0 | 1.3 | 0.9 |

| | pK13 | pK23 | pL13 | pL23 | pSE280 |
|---|---|---|---|---|---|
| TCE | 0 | 0 | 0 | 0 | 21.2 |
| cis-1,2-DCE | 0 | 0 | 0 | 0 | 19.9 |
| trans-1,2-DCE | 0 | 0 | 0 | 0 | 20.7 |
| 1,1-DCE | 0 | 0 | 0 | 0 | 19.8 |
| Toluene | 0 | 0 | 0 | 0 | 20.5 |
| Benzene | 0 | 0 | 0.3 | 0.1 | 21.0 |

(Unit: ppm)

Similarly, phenol, ortho-cresol, meta-cresol and para-cresol were introduced into respective 27.5 ml vials each containing 10 ml of the cell suspension, at a concentration of 50 ppm. Each vial was tightly sealed with a butyl rubber stopper and aluminum seal. The vials were shaken and incubated at 30° C. The quantities of the respective compounds in the liquid phase were determined by the amino antipyrine method with a spectrophotometer to determine their concentrations after 6 hours. The results are shown in Table 7. *E. coli* HB101(pSE280) was employed as a control and degradation was evaluated in the same manner.

TABLE 7

| | pK19 | pK29 | pL19 | pL29 | pK12 | pK22 | pL12 | pL22 |
|---|---|---|---|---|---|---|---|---|
| Phenol | 0 | 0 | 0 | 0 | 0 | 0 | 0 | 0 |
| Ortho-cresol | 0 | 0 | 0 | 0 | 0 | 0 | 0 | 0 |
| Meta-cresol | 0 | 0 | 0 | 0 | 0 | 0 | 0 | 0 |
| Para-cresol | 0 | 0 | 0 | 0 | 0 | 0 | 0 | 0 |

| | pK13 | pK23 | pL13 | pL23 | pSE280 |
|---|---|---|---|---|---|
| Phenol | 0 | 0 | 0 | 0 | 50.0 |
| Ortho-cresol | 0 | 0 | 0 | 0 | 51.1 |
| Meta-cresol | 0 | 0 | 0 | 0 | 52.3 |
| Para-cresol | 0 | 0 | 0 | 0 | 47.9 |

(Unit: ppm)

The above results confirm that *E. coli* HB101 transformants harboring toluene monooxygenase-expression vectors has an excellent ability to degrade aromatic compounds and chlorinated aliphatic hydrocarbon compounds. It is shown that transformants harboring pTrc99A- or pSE380-based expression vectors show more excellent degrading activity by IPTG induction.

EXAMPLE 9

TCE Degradation by *E. coli* HB101(pK22) and HB101(pK23) recombinant Strains in Soil (Without IPTG Induction)

E. coli HB101(pK22) and HB101(pK23) recombinant strains as described in Example 6 were respectively inoculated in 10 ml of LB medium and cultured at 37° C. overnight. Fifty grams of Sawara sieved sand (unsterilized) was placed in 68 ml vials each. Five ml of LB medium inoculated with the above seed culture to 100:1, was then added to the sand in each vial. Each vial was cotton-plugged, and incubated at 37° C. for 8 hours without shaking. After that, each vial was tightly sealed with a Teflon-coated butyl rubber stopper and aluminum seal. Gaseous TCE was introduced into the vials with a syringe to 20 ppm (supposing all TCE dissolved into the aqueous phase in the vial). The vials were incubated at 30° C. Quantitative analysis of TCE in the gas phase were carried out by gas chromatography after 6 hours to determine TCE concentrations. The results are shown in Table 8. E. coli HB101(pSE280) was employed as a control and evaluated in the same manner.

TABLE 8

|  | pK22 | pK23 | pSE280 |
|---|---|---|---|
| TCE | 0 | 2.4 | 20.8 |

(Unit: ppm)

The above results confirm that E. coli HB101 transformants harboring pK22 and pK23 also show an excellent TCE-degrading ability in soil. It is shown that transformant harboring pK23 (pSE380-based) expresses a lower degrading activity in a system not containing IPTG than that harboring pSE280-derived plasmid pK23, since the former contains lacIq.

EXAMPLE 10

TCE Degradation by E. coli HB101(pK22) or HB101(pK23) in Soil (With IPTG Induction)

The cells of E. coli HB101(pK22) and HB101(pK23) recombinant strains as described in Example 6 were respectively inoculated in 10 ml of LB medium and cultured at 37° C. overnight. Fifty grams of Sawara sieved sand (unsterilized) were placed in 68 ml vials each. Five ml of LB medium inoculated with the above seed culture to 100:1, was then added to the sand. Each vial was cotton-plugged, and incubated at 37° C. for 4 hours without shaking. Then 1 ml of a 10 mM IPTG solution was added to each vial. After that, each vial was tightly sealed with a Teflon-coated butyl rubber stopper and aluminum seal. Gaseous TCE was introduced into the vials with a syringe to 20 ppm (supposing all TCE dissolved into the aqueous phase in the vial). The vials were incubated at 30° C. Quantitative analysis of TCE in the gas phase were carried out by gas chromatography after 6 hours to determine TCE concentrations. The results are shown in Table 9. E. coli HB101(pSE280) was employed as a control and evaluated in the same manner.

TABLE 9

|  | pK22 | pK23 | pSE280 |
|---|---|---|---|
| TCE | 0 | 0 | 20.3 |

(Unit: ppm)

The above results confirm that E. coli HB101 transformants harboring pK22 and pK23 also show an excellent TCE-degrading ability in soil. It is shown that transformant harboring pK23 (pSE380-based) expresses higher degrading activity with IPTG induction.

EXAMPLE 11

TCE Degradation by E. coli HB101(pK22) or HB101(pK23) in Gas Phase (Without IPTG Induction)

The cells of respective recombinant strains, E. coli HB101 (pK22) and HB101(pK23) as described in Example 6, were inoculated in 100 ml of LB medium and cultured at 37° C. overnight. Aliquots (30 ml) of each seed culture were transferred into 68 ml vials, into which air which had passed through a saturation TCE solution was introduced at a flow rate of 20 ml/min for 10 minutes. Each vial was tightly sealed with a Teflon-coated butyl rubber stopper and aluminum seal, and shaking culture was conducted at 30° C. Quantitative analysis of TCE in the gas phase were carried out by gas chromatography to determine its concentration after 6 hours. The results are shown in Table 10. E. coli HB101(pSE280) was employed as a control and degradation was evaluated in the same manner.

TABLE 10

|  | pK22 | pK23 | pSE280 |
|---|---|---|---|
| TCE | 0 | 12.1 | 47.9 |

(Unit: ppm)

The above results confirm that recombinant E. coli HB101(pK22) or HB101(pK23) shows an excellent TCE-degrading ability also in the gas phase. It is shown that transformant harboring pK23 (pSE380-based) expresses a lower degrading activity in a system not containing IPTG than that harboring pSE280-derived plasmid pK23, since the former contains lacIq.

EXAMPLE 12

TCE Degradation by recombinant E. coli HB101(pK22) and HB101(pK23) in Gas Phase (With IPTG Induction)

E. coli (HB101) recombinant strains each harboring pK22 or pK23 as described in Example 6 were respectively inoculated into 100 ml of LB medium and cultured at 37° C. to reach $OD_{600}$ of about 0.8, and then IPTG was added to 1 mM concentration followed by further incubation at 37 C. for 5 hours. Aliquots (30 ml) of the cell suspension were transferred into 68 ml vials, into which air which had passed through in a saturated TCE solution was introduced at a flow rate of 20 ml/min for 10 minutes. Each vial was tightly sealed with a Teflon-coated butyl rubber stopper and aluminum seal, and shaking culture was conducted at 30° C. Quantitative analysis of TCE in the gas phase were carried out by gas chromatography to determine its concentration after 6 hours. The results are shown in Table 11. E. coli HB101(pSE280) was employed as a control and degradation was evaluated in the same manner.

TABLE 11

|  | pK22 | pK23 | pSE280 |
|---|---|---|---|
| TCE | 0 | 0 | 54.2 |

(Unit: ppm)

The above results confirm that recombinant E. coli HB101(pK22) or HB101(pK23) shows an excellent TCE-degrading ability also in the gas phase, and show that transformant harboring pK23 (pSE380-based) expresses higher degrading activity with IPTG induction.

EXAMPLE 13
Introduction of Recombinant Plasmid containing Toluene Monooxygenase Gene into *Vibrio* sp. strain KB1

The toluene monooxygenase gene beginning from the second ATG of tomK (base number 234–236) was transferred from the recombinant plasmid pK29 of Example 6 (recombinant pTrc99A containing the gene) into a vector pBBR1 22 (Mo Bi Tec) having a wide host range replication region not belonging to an incompatible group of IncP, IncQ, and IncW. This recombinant plasmid was introduced in *Vibrio* sp. strain KB1, and its ability to degrade aromatic compounds and chlorinated aliphatic hydrocarbon compounds was evaluated.

First, a wide host range recombinant plasmid was constructed. An about 7.0-kb fragment containing the toluene monooxygenase gene, a trc promoter, and a rrnB terminator was cut out from pK29 using the restriction enzymes HpaI (Takara Shuzo Co., Ltd.) and SmaI (Takara Shuzo Co., Ltd.). This fragment of about 7.0 kb does not contain the lacIq sequence. As a vector of a wide host range, pBBR122 was employed. pBBR122 was completely digested with the restriction enzyme SmaI (Takara Shuzo Co., Ltd.). The 7.0 kb fragment containing the toluene monooxygenase gene, a trc promoter, and an rrnB terminator prepared as described above was ligated to the SmaI restriction site of the pBBR122 using DNA Ligation Kit Ver. 2 (Takara Shuzo Co., Ltd.) and the recombinant plasmid thus constructed was introduced into *E. coli* HB101 (Takara Shuzo Co., Ltd.). The cells of the *E. coli* thus treated were applied on LB plate containing 50 $\mu$g/ml of chloramphenicol as a selection agent. When the colonies on the plate grew to an appropriate size, the colonies were transferred by replica printing onto an LB plate containing 50 $\mu$g/ml of kanamycin as a selection agent. Transformants that could proliferate on the plate with chloramphenicol but not on the plate with kanamycin were selected, and cultured in LB medium at 37° C. overnight, to extract plasmid DNA from the cells by the alkaline method. After checking the plasmids, transformants harboring a recombinant plasmid where the 7.0 kb fragment was correctly inserted into the SmaI site of the pBBR122 were obtained. The recombinant plasmid thus obtained was about 12.3 kb in length and designated as pK29bbr.

The SOB medium shown below was employed for liquid culture of *Vibrio* sp. strain KB1. Chloramphenicol was used at a concentration of 50 $\mu$g/ml as a selection agent and the culture temperature was 30° C. The recombinant plasmid pK29 was introduced into *Vibrio* sp. strain KB1 cells by electroporation using a gene pulsar (Bio-Rad). The recombinant plasmid pK29bbr was stably retained after introduction into *Vibrio* sp. strain KB1. SOB medium:

Trypton: 20 g
Yeast extract: 5 g
NaCl: 0.5 g
250 mM KCl: 10 ml
Distilled water (to 990 ml)
pH 7.0

The above solution was sterilized by autoclaving and cooled to room temperature, to which 10 ml of a 2 M Mg solution (1 M $MgSO_{4.7}H_2O$ + 1 M $MgCl_{2.6}H_2O$) separately sterilized by autoclaving was added.

EXAMPLE 14
Ability of *Vibrio* sp. KB1(pK29bbr) to Degrade Aromatic Compounds and Chlorinated Aliphatic Hydrocarbon Compounds The cells of *Vibrio* sp. KB1(pK29bbr) were inoculated in 100 ml of SOB medium, cultured at 30° C. overnight, harvested, washed, and then suspended in 100 ml of M9 (containing 6.2 g of $Na_2HPO_4$, 3.0 g of $KH_2PO_4$, 0.5 g of NaCl, and 1.0 g of $NH_4Cl$ per liter) supplemented with a mineral stock solution (3 ml to 1 liter of M9 medium).

Ten ml of the suspension was placed in respective 27.5 ml vials and each vial was tightly sealed with a Teflon-coated butyl rubber stopper and aluminum seal. Then, gaseous trichloroethylene (TCE), cis-1,2-dichloroethylene (cis-1,2-DCE), trans-1,2-dichloroethylene (trans-1,2-DCE), 1,1-dichloroethylene (1,1-DCE), toluene, and benzene were added to respective vials with a syringe to a concentration of 20 ppm (supposing all of the introduced substance dissolved in the aqueous phase in the vial). The vials were shaken and incubated at 30° C. The concentrations of the respective compounds in the gas phase after 6 hour incubation were measured by gas chromatography. The results are shown in Table 12. *Vibrio* sp. KB1(pBBR122) was tested as a control and degradation was evaluated in the same manner.

TABLE 12

|  | KB1 (pK29bbr) | KB1 (pBBR122) |
| --- | --- | --- |
| TCE | 0 | 19.1 |
| cis-1,2-DCE | 0 | 20.2 |
| trans-1,2-DCE | 0 | 21.3 |
| 1-1, DCE | 0 | 19.2 |
| Toluene | 0 | 19.8 |
| Benzene | 0 | 21.0 |

(Unit: ppm)

Similarly, to 10 ml of the prepared cell suspension in a 27.5-ml vial, phenol, ortho-cresol, meta-cresol, and para-cresol were added to 50 ppm, respectively. The vial was tightly sealed with a butyl rubber stopper and aluminum seal, and then shaken and incubated at 30° C. The quantities of the respective compounds in the liquid phase were measured by the amino antipyrine method with a spectrophotometer to obtain their concentrations after 6 hours. The results are shown in Table 13. *Vibrio* species strain KB1 containing only pBBR122 was employed as a control and degradation was evaluated in a similar system.

Similarly, phenol, ortho-cresol, meta-cresol and para-cresol were introduced at a concentration of 50 ppm into respective 27.5 ml vials each containing 10 ml of the cell suspension. Each vial was tightly sealed with a butyl rubber stopper and aluminum seal, and shaken and incubated at 30° C. The quantities of the respective compounds in the liquid phase were determined by the amino antipyrine method using a spectrophotometer to determine their concentrations after 6 hours. The results are shown in Table 13. *Vibrio* sp. KB1(pBBR122) was tested as a control and degradation was evaluated in the same manner.

TABLE 13

|  | KB1 (pK29bbr) | KB1 (pBBR122) |
| --- | --- | --- |
| Phenol | 0 | 51 |
| Ortho-cresol | 0 | 50 |
| Meta-cresol | 0 | 49 |
| Para-cresol | 0 | 50 |

(Unit: ppm)

The above results show that the recombinant *Vibrio* sp. strain KB1 harboring pK29bbr can constitutively express the ability to degrade aromatic compounds and chlorinated aliphatic hydrocarbon compounds.

EXAMPLE 15
Degradation of TCE by Recombinant *Vibrio* sp. KB1 (pK29bbr) in Soil

*Vibrio* sp. KB1(pK29bbr) recombinant strain as described in Example 13 was inoculated in 10 ml of SOB medium and cultured at 30° C. overnight. Fifty grams of Sawara sieved sand (unsterilized) was placed in each 68 ml vial. Five ml of SOB medium inoculated with the above seed culture to 100:1 was then added to the sand in each vial. Each vial was cotton-plugged and incubated at 30° C. for 12 hours without shaking. After that, each vial was tightly sealed with a Teflon-coated butyl rubber stopper and aluminum seal. Gaseous TCE was introduced into the vials with a syringe to 20 ppm supposing all TCE dissolved into the aqueous phase in the vial). The vials were incubated at 30° C. Quantitative analysis of TCE in the gas phase were carried out by gas chromatography after 6 hours to determine TCE concentrations. The results are shown in Table 14. *Vibrio* sp. KB1 (pBBR122) was tested as a control and degradation was evaluated in the same manner.

TABLE 14

|  | KB1 (pK29bbr) | KB1 (pBBR122) |
|---|---|---|
| TCE | 0 | 20.2 |

(Unit: ppm)

The above results show that the recombinant *Vibrio* sp. KB1(pK29bbr) can constitutively express the ability to degrade TCE also in soil.

EXAMPLE 16
Degradation of TCE by Recombinant *Vibrio* sp. KB1 (pK29bbr) in Gas Phase The cells of recombinant *Vibrio* sp. KB1(pK29bbr) as described in Example 13 were inoculated in 100 ml of SOB medium and cultured at 30° C. overnight. Aliquots (30 ml) of the seed culture were transferred into 68 ml vials, into which air which had passed through a saturation TCE solution was introduced at a flow rate of 20 ml/min for 10 minutes. Each vial was tightly sealed with a Teflon-coated butyl rubber stopper and aluminum seal, and shaking culture was conducted at 30° C. Quantitative analysis of TCE in the gas phase were carried out by gas chromatography to determine its concentration after 6 hours. The results are shown in Table 15. *Vibrio* sp. KB1(pBBR1 22) was employed as a control and degradation was evaluated in the same manner.

TABLE 15

|  | KB1 (pK29bbr) | KB1 (pBBR122) |
|---|---|---|
| TCE | 0 | 52.1 |

(Unit: ppm)

The above results show that the recombinant *Vibrio* sp. KB1(pK29bbr) can constitutively express the ability to degrade TCE also in the gas phase.

According to the present invention, a DNA fragment carrying a toluene monooxygenase gene with an excellent ability to degrade aromatic compounds and chlorinated aliphatic hydrocarbon compounds can be obtained. In addition, a novel recombinant plasmid containing the DNA fragment as a whole or a part thereof that can be utilized to obtain a transformant capable of degrading aromatic compounds and/or chlorinated aliphatic hydrocarbon compounds can be obtained. Further, a transformant harboring the plasmid and can be utilized to degrade aromatic compounds and/or chlorinated aliphatic hydrocarbon compounds can be obtained. Furthermore, a practical method for environmental remediation that can efficiently degrade either aromatic compounds and/or chlorinated aliphatic hydrocarbon compounds by utilizing the transformant.

What is claimed is:

1. An isolated DNA fragment of about 5.8 Kb containing a toluene monooxygenase gene, having 1 BamHI restriction site, 2 EcoRI restriction sites, 1 HpaI restriction site, 1 KpnI restriction site, 1 NcoI restriction site, 1 NspV restriction site, 1 SacI restriction site, 2 SmaI restriction sites, 3 SphI restriction sites, 2 XhoI restriction sites, no ClaI restriction site, no DraI restriction site, no EcoRV restriction site, no HindIII restriction site, no NdeI restriction site, no NheI restriction site, no PvuII restriction site, no ScaI restriction site, no Sse8387I restriction site, no StuI restriction site, and no XbaI restriction site, and having a restriction map of:

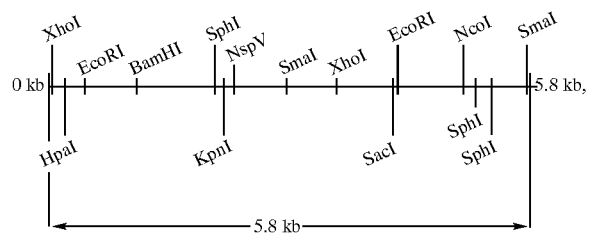

said isolated DNA fragment derived from *Burkholderia cepacia* KK01.

2. A DNA fragment isolated from *Burkholderia cepacia* KK01 wherein the DNA fragment has a nucleotide sequence of SEQ ID NO: 1.

3. An isolated DNA fragment having a nucleotide sequence of SEQ ID NO. 1, or a 100% complementary sequence of SEQ ID NO. 1, wherein said nucleotide sequence includes deletion, substitution or addition of one base, and wherein said DNA fragment encodes a toluene monooxygenase.

4. A recombinant DNA comprising a vector enabling maintenance or replication in a host, said vector including a DNA fragment according to any one of claims 1 to 3.

5. The recombinant DNA according to claim 4, wherein the vector can be maintained or replicated in a bacterium.

6. An isolated DNA fragment containing a region encoding a toluene monooxygenase, the region comprising a first sequence encoding a polypeptide TomL having an amino acid sequence of SEQ ID NO: 3, a second sequence encoding a polypeptide TomM having an amino acid sequence of SEQ ID NO: 4, a third sequence encoding a polypeptide TomN having an amino acid sequence of SEQ ID NO: 5, a fourth sequence encoding a polypeptide TomO having an amino acid sequence of SEQ ID NO: 6, and a fifth sequence encoding a polypeptide TomP having an amino acid sequence of SEQ ID NO: 7, and the first to fifth sequences are aligned so that expressed TomL-TomP polypeptides can form said toluene monooxygenase.

7. An isolated DNA fragment according to claim 6, wherein no spacer sequence is present between the first to fifth sequences.

8. An isolated DNA fragment according to claim 6, wherein at least one spacer sequence is present between the first to fifth sequences.

9. An isolated DNA fragment according to claim 6, 7 or 8 further comprising a sequence encoding a polypeptide TomQ having an amino acid sequence of SEQ ID NO: 8.

10. An isolated DNA fragment containing a region encoding a toluene monooxygenase, wherein the region comprises a first sequence having a nucleotide sequence from nucleotide 463 to nucleotide 1455 of SEQ ID NO: 1 or a 100% complementary sequence thereof, encoding a polypeptide TomL having an amino acid sequence of SEQ ID NO:3, a second sequence having a nucleotide sequence from nucleotide 1495 to nucleotide 1761 of SEQ ID NO: 1 or a 100% complementary sequence thereof, encoding a polypeptide TomM having an amino acid sequence of SEQ ID NO: 4, a third sequence having a nucleotide sequence from nucleotide 1803 to nucleotide 3350 of SEQ ID NO: 1 or a 100% complementary sequence thereof, encoding a polypeptide TomN having an amino acid sequence of SEQ ID NO: 5, a fourth sequence having a nucleotide sequence from nucleotide 3428 to nucleotide 3781 of SEQ ID NO: 1 or a 100% complementary sequence thereof, encoding a polypeptide TomO having an amino acid sequence of SEQ ID NO: 6, and a fifth sequence having a nucleotide sequence from nucleotide 3810 to nucleotide 4871 of SEQ ID NO: 1 or a 100% complementary sequence thereof, encoding a polypeptide TomP having an amino acid sequence of SEQ ID NO: 7, wherein the first to fifth sequence include substitution of one base and wherein the first to fifth sequences are aligned so that expressed polypeptides can form said toluene monooxygenase.

11. An isolated DNA fragment comprising a region having a nucleotide sequence from nucleotide 234 to nucleotide 443 of SEQ ID NO: 1 or a 100% complementary sequence thereof, wherein said nucleotide sequence includes deletion, substitution or addition of one base, and wherein said DNA fragment encodes a polypeptide having a property to enhance toluene monooxygenase activity.

12. A recombinant DNA comprising a vector, wherein said vector contains a promoter which is functionally ligated to a DNA fragment according to any one of claims 6, 7, 8 or 9 to enable expression of the toluene monooxygenase encoded by the DNA fragment.

13. The recombinant DNA according to claim 12 wherein the promoter and the vector can function in a bacterium.

14. A recombinant DNA comprising an expression vector comprising a first promoter functionally linked to a first DNA fragment comprising a region having a nucleotide sequence from nucleotide 234 to nucleotide 443 of SEQ ID NO: 1 or a 100% complementary sequence thereof, wherein said nucleotide sequence includes deletion, substitution or addition of one base, and wherein said DNA fragment encodes a polypeptide having a property to enhance toluene monooxygenase activity, and a second promoter functionally linked to a second DNA fragment, wherein the second DNA fragment is a DNA fragment according to any one of claims 6, 7, 8 or 9.

15. The recombinant DNA according to claim 14, wherein the first and second promoters and the vector can function in a bacterium.

16. A transformant obtained by introducing a recombinant DNA into a host microorganism, the recombinant DNA comprising a vector enabling maintenance or replication in a host and a DNA fragment of about 5.8 Kb containing a toluene monooxygenase gene having 1 BamHI restriction site, 2 ECOR1 restriction sites, 1 HpaI restriction site, 1 KpuI restriction site, 1 NcoI restriction site, 1 NspV restriction site, 1 SacI restriction site, 2 SmaI restriction sites, 3 SphI restriction sites, 2 XhoI restriction sites, no ClaI restriction site, no DraI restriction site, no EcoRV restriction site, no HindIII restriction site, no NdeI restriction site, no NheI restriction site no PvuII restriction site, no ScaI restriction site, no Sse83871 restriction site, no StuI restriction site, and no XbaI restriction site, said DNA fragment derived from *Burkholderia cepacia* KK01.

17. The transformant according to claim 16, wherein the host microorganism is a bacterium.

18. A transformant obtained by introducing a recombinant DNA into a host microorganism, where the recombinant DNA comprises a vector enabling maintenance or replication in a host, said vector including a DNA fragment ligated thereto, wherein the DNA fragment is a fragment of a nucleotide sequence of SEQ ID NO: 1 or a 100% complementary sequence of SEQ ID NO: 1 and is 4.9 kb or less, and wherein the DNA fragment includes deletion, substitution or addition of one base and encodes a toluene monooxygenase.

19. The transformant according to claim 18, wherein the host microorganism is a bacterium.

20. A transformant obtained by introducing a recombinant DNA comprising a vector, a promoter and a DNA fragment into a host microorganism where the DNA fragment contains a region encoding a toluene monooxygenase, the region comprising a first sequence encoding a polypeptide TomL having an amino acid sequence of SEQ ID NO: 3, a second sequence encoding a polypeptide TomM having an amino acid sequence of SEQ ID NO: 4, a third sequence encoding a polypeptide TomN having an amino acid sequence of SEQ ID NO: 5, a fourth sequence encoding a polypeptide TomO having an amino acid sequence of SEQ ID NO: 6, and a fifth sequence encoding a polypeptide TomP having an amino acid sequence of SEQ ID NO: 7, and the first to fifth sequences are aligned so that expressed TomL-TomP polypeptides can form said toluene monooxygenase;

wherein the promoter and the DNA fragment are functionally linked enabling expression of the toluene monooxygenase encoded by the DNA fragment.

21. The transformant according to claim 20, wherein said host microorganism is a bacterium.

22. A method for producing a toluene monooxygenase, comprising the steps of:

culturing a transformant according to any one of claims 16, 18 or 20 in a medium; and collecting the expressed toluene monooxygenase.

23. A method for degrading at least one of a chlorinated aliphatic hydrocarbon compound and an aromatic compound in a medium comprising a step of contacting at least one of a chlorinated aliphatic hydrocarbon compound and an aromatic compound with the transformant according to any one of claims 16, 18 or 20.

24. The degradation method according to claim 23, wherein the medium is an aqueous medium.

25. The degradation method according to claim 23, wherein the medium is soil.

26. The degradation method according to claim 23, wherein the medium is air.

27. The degradation method according to claim 23, wherein the chlorinated aliphatic hydrocarbon compound is either trichloroethylene (TCE) or dichloroethylene (DCE).

28. The degradation method according to claim 23, wherein the aromatic compound is selected from the group consisting of toluene, benzene, phenol, and cresol.

29. A method for cleaning a medium polluted with at least one of a chlorinated aliphatic hydrocarbon compound and aromatic compound comprising a step of contacting at least one of a chlorinated aliphatic hydrocarbon compound and an aromatic compound, with the transformant according to any one of claims 16, 18 or 20.

30. The cleaning method according to claim 29 wherein the medium is an aqueous medium.

31. The cleaning method according to claim 29 wherein the medium is soil.

32. The cleaning method according to claim 29 wherein the medium is air.

33. The cleaning method according to claim 29 wherein the chlorinated aliphatic hydrocarbon compound is either trichloroethylene (TCE) or dichloroethylene (DCE).

34. The cleaning method according to claim 29 wherein the aromatic compound is selected from the group consisting of toluene, benzene, phenol, and cresol.

35. A method for remedying an environment polluted with a pollutant being a chlorinated aliphatic hydrocarbon compound or an aromatic compound, comprising a step of contacting the pollutant with the transformant according to any one of claims 16, 18 or 20.

36. The remediation method according to claim 35 wherein the environment is made of an aqueous medium.

37. The remediation method according to claim 36 wherein the polluted aqueous medium is brought into contact with a carrier holding the transformant.

38. The remediation method according to claim 37 wherein the contact is carried out by placing the carrier holding the transformant in a container, introducing the polluted aqueous medium from one side of the container, and discharging the remedied aqueous medium from another side.

39. The remediation method according to claim 35, wherein the environment is made of soil.

40. The remediation method according to claim 39 being carried out by introducing an aqueous medium containing the transformant into the polluted soil and supplying nutrients and/or oxygen for proliferation of the transformant in the polluted soil.

41. The remediation method according to claim 40 wherein the transformant is introduced in the soil with applying pressure through an injection well provided in the polluted soil.

42. The remediation method according to claim 39 wherein the polluted soil is introduced in a liquid phase containing the transformant.

43. The remediation method according to claim 39 wherein the polluted soil is brought into contact with a carrier holding the transformant.

44. The remediation method according to claim 35 wherein the environment is made of air.

45. The remediation method according to claim 44 wherein the polluted air is introduced into a liquid phase containing the transformant.

46. The remediation method according to claim 44 wherein the polluted air is brought into contact with a carrier holding the transformant.

47. The remediation method according to claim 46 wherein contact is carried out by placing the carrier holding the transformant in a container, introducing polluted air from one side of the container, and discharging cleaned air from another side.

48. The remediation method according to claim 35 wherein the chlorinated aliphatic hydrocarbon compound is either trichloroethylene (TCE) or dichloroethylene (DCE).

49. The remediation method according to claim 35, wherein the aromatic compound is selected from the group consisting of toluene, benzene, phenol, and cresol.

* * * * *

UNITED STATES PATENT AND TRADEMARK OFFICE
CERTIFICATE OF CORRECTION

PATENT NO. : 6,864,074 B2
DATED : March 8, 2005
INVENTOR(S) : Tetsuya Yano et al.

It is certified that error appears in the above-identified patent and that said Letters Patent is hereby corrected as shown below:

Title page,
Item [*] Notice, insert:
-- This patent issued on a continued prosecution application filed under 37 CFR 1.53(d), and is subject to the twenty year patent term provisions of 35 U.S.C. 154(a)(2). --.
Item [56], References Cited, OTHER PUBLICATIONS,
"Hanson" reference, "et al/." should read -- et al. --;
"Negoro" reference, "vols. 28/27," should read -- Applied Biochemistry and Biotechnology, vols. 28/27, --;
"Wackett" reference, "Oxugenases:" should read -- Oxygenases: --; and
"Beam" reference, "microbiol.," should read -- Microbiol., --.

Column 1,
Line 56, "have" should read -- has --.

Column 2,
Line 10, "*Alcaligenes eutrophus* 3 MP 134" should read -- *Alcaligenes eutrophus* JMP134 --.

Column 3,
Line 14, "While," should read -- Meanwhile, --;
Line 50, "has" should read -- have --; and
Line 52, "an d" should read -- and --.

Column 4,
Line 7, "resent" should read -- present --; and
Line 33, "resent." should read -- present. --.

Column 6,
Lines 31 and 64, "loose" should read -- lose --.

Column 7,
Line 12, "EcORV" should read -- EcoRV --.

Column 8,
Line 29, "loose" should read -- lose --.

UNITED STATES PATENT AND TRADEMARK OFFICE
CERTIFICATE OF CORRECTION

PATENT NO. : 6,864,074 B2
DATED : March 8, 2005
INVENTOR(S) : Tetsuya Yano et al.

It is certified that error appears in the above-identified patent and that said Letters Patent is hereby corrected as shown below:

Column 9,
Line 12, "deaminase:" should read -- deaminase: – --;
Line 33, "L-(+j-arabinose: +" should read -- L-(+)-arabinose: + --;
Line 41, "litter)" should read -- liter) --; and
Line 61, "catechol-which" should read -- catechol which --.

Column 10,
Line 37, "enables" should read -- enable --.

Column 11,
Line 50, "*Moraxella.*" should read -- *Moraxella,* --.

Column 13,
Line 18, "BP-6923." should read -- BP-6923) --; and
Line 58, "BP-6913." should read -- BP-6913) --.

Column 14,
Line 31, "BP-6914." should read -- BP-6914) --; and
Line 40, "H2 S(—)" should read -- $H_2$ S(—) --.

Column 15,
Line 59, "and a" should read -- and an --; and
Line 63, "litter)" should read -- liter) --.

Column 16,
Line 48, "the filled" should read -- then filled --; and
Line 54, "it can" should read -- there can --.

Column 17,
Line 9, "introducing" should read -- introduce --;
Line 31, "it can" should read -- there can --;
Line 49, "promote" should read -- promotes --; and
Line 64, "it can" should read -- there can --.

Column 18,
Line 23, "there is" should read -- there are --;
Line 24, "case" should read -- cases --; and
Line 25, "exhibit." should read -- exhibited. --.

UNITED STATES PATENT AND TRADEMARK OFFICE
CERTIFICATE OF CORRECTION

PATENT NO. : 6,864,074 B2
DATED : March 8, 2005
INVENTOR(S) : Tetsuya Yano et al.

It is certified that error appears in the above-identified patent and that said Letters Patent is hereby corrected as shown below:

Column 21,
Line 22, "ABamHI" should read -- ΔBamHI --;
Line 31, "pUCIB" should read -- pUC18 --;
Line 53, "pKK01AEcoRI" should read -- pKK01ΔEcoRI --;
Line 54, "pKK0lAEcoRl" should read -- pKK01ΔEcoRl --; and "E, coli" should read -- *E. coli* --; and
Line 55, "pKK01AEcoR1" should read -- pKK01ΔEcoR1 --.

Column 22,
Line 29, "tomM S7 encoding" should read -- tomM encoding --.

Column 25,
Line 52, "harboring" should read -- Harboring --.

Column 26,
Line 58, "has" should read -- have --; and
Line 66, "recombinant" should read -- Recombinant --.

Column 27,
Line 5, "was placed" should read -- were placed --.

Column 28,
Line 37, "recombinant" should read -- Recombinant --.

Column 29,
Line 2, "containing" should read -- Containing --; and
Line 3, "strain" should read -- Strain --.

Column 30,
Line 5, "was placed" should read -- were placed --.

Column 31,
Line 7, "was placed" should read -- were placed --; and
Line 15, "were carried" should read -- was carried --.

Column 32,
Line 7, "were carried" should read -- was carried --; and
Line 36, "transformant." should read -- transformant can be obtained. --.

UNITED STATES PATENT AND TRADEMARK OFFICE
CERTIFICATE OF CORRECTION

PATENT NO. : 6,864,074 B2
DATED : March 8, 2005
INVENTOR(S) : Tetsuya Yano et al.

It is certified that error appears in the above-identified patent and that said Letters Patent is hereby corrected as shown below:

Column 57,
Line 3, "sequence" should read -- sequences --;
Line 42, "KpuI" should read -- KpnI --; and
Line 47, "site no" should read -- site, no --.

Column 58,
Line 44, "compound," should read -- compound --.

Signed and Sealed this

Fourteenth Day of February, 2006

JON W. DUDAS
*Director of the United States Patent and Trademark Office*

SEQUENCE LISTING

```
<160> NUMBER OF SEQ ID NOS: 13

<210> SEQ ID NO 1
<211> LENGTH: 5828
<212> TYPE: DNA
<213> ORGANISM: Burkholderia cepacia
<220> FEATURE:
<221> NAME/KEY: CDS
<222> LOCATION: (234)..(443)
<223> OTHER INFORMATION: tomK
<220> FEATURE:
<221> NAME/KEY: CDS
<222> LOCATION: (463)..(1455)
<223> OTHER INFORMATION: tomL
<220> FEATURE:
<221> NAME/KEY: CDS
<222> LOCATION: (1495)..(1761)
<223> OTHER INFORMATION: tomM
<220> FEATURE:
<221> NAME/KEY: CDS
<222> LOCATION: (1803)..(3350)
<223> OTHER INFORMATION: tomN
<220> FEATURE:
<221> NAME/KEY: CDS
<222> LOCATION: (3428)..(3781)
<223> OTHER INFORMATION: tomO
<220> FEATURE:
<221> NAME/KEY: CDS
<222> LOCATION: (3810)..(4871)
```

<223> OTHER INFORMATION: tomP
<220> FEATURE:
<221> NAME/KEY: CDS
<222> LOCATION: (4876)..(5229)
<223> OTHER INFORMATION: tomQ

<400> SEQUENCE: 1

```
gatcatttca tcaaatgcgc tcgagcgggt tgctcaaatg atgaaaaagg ccaccggaca      60
tgggtttcgg cacgatcgcc ggcgggcgtt ttccgttctg gttaaccgcc attgtgggtc     120
gcgaaattta acttcgcgtc agggctttcc ctgaattatc gagattttt gctgcctggg     180 tcgaacgtgg cacggatgct gcattgaagt ccggcatgga ggcgacaccg atc atg        236
                                                         Met
                                                           1 aat cag cac ccc acc gat ctt tcc ccg ttc gat ccc ggc cgc aag tgc       284
Asn Gln His Pro Thr Asp Leu Ser Pro Phe Asp Pro Gly Arg Lys Cys
        5                  10                  15 gtc cgc gtg acc ggc acg aac gcg cgc ggc ttc gtc gaa ttc gag ctg       332
Val Arg Val Thr Gly Thr Asn Ala Arg Gly Phe Val Glu Phe Glu Leu
 20                  25                  30 tcg atc ggc ggc gcg ccg gaa ctg tgc gtc gag ctg acg ttg tct cct       380
Ser Ile Gly Gly Ala Pro Glu Leu Cys Val Glu Leu Thr Leu Ser Pro
 35                  40                  45 gcc gcc ttc gat gcg ttc tgc cgc gaa cag cag gtc acg cgg ctc gac       428
Ala Ala Phe Asp Ala Phe Cys Arg Glu Gln Gln Val Thr Arg Leu Asp
 50                  55                  60                  65 gtc gaa gcg aac cca tgaccttgag gagcaagaa gtg acc atc gag ctg aag      480
Val Glu Ala Asn Pro              Met Thr Ile Glu Leu Lys
             70                                      75 aca gtc gac atc aag ccg ctc cgg cac acc ttt gcg cat gtc gcg cag       528
Thr Val Asp Ile Lys Pro Leu Arg His Thr Phe Ala His Val Ala Gln
             80                  85                  90 aac atc ggc ggc gac aag acg gcg acg cgc tac cag gaa ggc atg atg       576
Asn Ile Gly Gly Asp Lys Thr Ala Thr Arg Tyr Gln Glu Gly Met Met
         95                 100                 105 ggc gcg cag ccc cag gag aac ttc cat tac cgg ccg acc tgg gac ccg       624
Gly Ala Gln Pro Gln Glu Asn Phe His Tyr Arg Pro Thr Trp Asp Pro
110                 115                 120 gac tac gag atc ttc gat ccg tcg cgc tcg gcg atc cgg atg gcg aac       672
Asp Tyr Glu Ile Phe Asp Pro Ser Arg Ser Ala Ile Arg Met Ala Asn
125                 130                 135                 140 tgg tac gcg ttg aag gat ccg cgc cag ttc tac tac gcg tcg tgg gcg       720
Trp Tyr Ala Leu Lys Asp Pro Arg Gln Phe Tyr Tyr Ala Ser Trp Ala
                145                 150                 155 acc acg cgg gcg cgc cag cag gat gcg atg gag tcg aac ttc gag ttc       768
Thr Thr Arg Ala Arg Gln Gln Asp Ala Met Glu Ser Asn Phe Glu Phe
                160                 165                 170 gtc gaa tcg cgc cgg atg atc ggc ctg atg cgc gac gac gtg gcc gcg       816
Val Glu Ser Arg Arg Met Ile Gly Leu Met Arg Asp Asp Val Ala Ala
                175                 180                 185 cgg gcg ctc gac gtg ctg gtg ccg ctg cgc cac gcc gcg tgg ggc gcg       864
Arg Ala Leu Asp Val Leu Val Pro Leu Arg His Ala Ala Trp Gly Ala
    190                 195                 200 aac atg aac aac gcg cag atc tgc gcg ctc ggc tac ggc acg gtg ttc       912
Asn Met Asn Asn Ala Gln Ile Cys Ala Leu Gly Tyr Gly Thr Val Phe
205                 210                 215                 220 acc gcg ccc gcg atg ttc cat gcg atg gac aac ctc ggc gtc gcg caa       960
Thr Ala Pro Ala Met Phe His Ala Met Asp Asn Leu Gly Val Ala Gln
                225                 230                 235 tac ctc acg cgt ctc gcg ctc gcg atg gcc gag ccc gac gtg ctg gag      1008
Tyr Leu Thr Arg Leu Ala Leu Ala Met Ala Glu Pro Asp Val Leu Glu
```

-continued

```
                Tyr Leu Thr Arg Leu Ala Leu Ala Met Ala Glu Pro Asp Val Leu Glu
                            240                 245                 250 gcg gcc aag gcg acc tgg acc cgc gac gcc gcc tgg cag ccg ctg cgc              1056
Ala Ala Lys Ala Thr Trp Thr Arg Asp Ala Ala Trp Gln Pro Leu Arg
            255                 260                 265 cgc tac gtc gag gac acg ctg gtc gtc gcc gat ccg gtc gag ctg ttc              1104
Arg Tyr Val Glu Asp Thr Leu Val Val Ala Asp Pro Val Glu Leu Phe
        270                 275                 280 atc gcg cag aac ctc gcg ctc gac ggc ctg ctg tat ccg ctc gtc tac              1152
Ile Ala Gln Asn Leu Ala Leu Asp Gly Leu Leu Tyr Pro Leu Val Tyr
285                 290                 295                 300 gac cgc ttc gtc gac gaa cgg atc gcg ctc gaa ggc ggc tcg gca gtc              1200
Asp Arg Phe Val Asp Glu Arg Ile Ala Leu Glu Gly Gly Ser Ala Val
                305                 310                 315 gcg atg ctg acc gcg ttc atg ccc gaa tgg cac acc gag tcg aac cgc              1248
Ala Met Leu Thr Ala Phe Met Pro Glu Trp His Thr Glu Ser Asn Arg
            320                 325                 330 tgg atc gac gcg gtc gtg aag acg atg gcc gcc gaa tcc gac gac aac              1296
Trp Ile Asp Ala Val Val Lys Thr Met Ala Ala Glu Ser Asp Asp Asn
        335                 340                 345 cgc gcg ctg ctc gcc cgc tgg aca cgc gac tgg tcc gcg cgc gcc gag              1344
Arg Ala Leu Leu Ala Arg Trp Thr Arg Asp Trp Ser Ala Arg Ala Glu
350                 355                 360 gcg gca ctg gca ccg gtg gcg gca cgc gcg ctg cag gat gcc ggg cgc              1392
Ala Ala Leu Ala Pro Val Ala Ala Arg Ala Leu Gln Asp Ala Gly Arg
365                 370                 375                 380 gcg gcg ctc gac gaa gtg cgc gag cag ttc cac gca cgc gcg gcc agg              1440
Ala Ala Leu Asp Glu Val Arg Glu Gln Phe His Ala Arg Ala Ala Arg
                385                 390                 395 ctc ggc atc gcg ctc tgacgacggg aatcctccct taacccaagg aatgccagc              1494
Leu Gly Ile Ala Leu
            400 atg tcc aac gta ttc atc gcc ttt cag gcc aat gag gac tcc aga ccg              1542
Met Ser Asn Val Phe Ile Ala Phe Gln Ala Asn Glu Asp Ser Arg Pro
            405                 410                 415 atc gtg gat gcg atc gtc gcc gac aac ccg cgc gcg gtg gtg gtc gag              1590
Ile Val Asp Ala Ile Val Ala Asp Asn Pro Arg Ala Val Val Val Glu
        420                 425                 430 tcg ccc ggc atg gtc aag atc gac gcg ccg gac cgg ctg acg atc cgc              1638
Ser Pro Gly Met Val Lys Ile Asp Ala Pro Asp Arg Leu Thr Ile Arg
    435                 440                 445 cgc gaa acg atc gag gaa ctg acc ggc acg cgc ttc gac ctg cag cag              1686
Arg Glu Thr Ile Glu Glu Leu Thr Gly Thr Arg Phe Asp Leu Gln Gln
450                 455                 460                 465 ctc cag gtc aac ctg atc acg ctg tca ggc cac atc gac gag gac gac              1734
Leu Gln Val Asn Leu Ile Thr Leu Ser Gly His Ile Asp Glu Asp Asp
                470                 475                 480 gac gag ttc acg ctg agc tgg tcg cac tgaacgccgc gccacgcgca                    1781
Asp Glu Phe Thr Leu Ser Trp Ser His
            485                 490 ccgacaacac cggagacacg a atg gac acg cca acg ctc aag aaa aaa ctc              1832
                        Met Asp Thr Pro Thr Leu Lys Lys Lys Leu
                                            495                 500 ggc ctg aag gac cgc tac gcg gca atg acg cgc ggc ctc ggc tgg gag              1880
Gly Leu Lys Asp Arg Tyr Ala Ala Met Thr Arg Gly Leu Gly Trp Glu
            505                 510                 515 acg acc tac cag ccg atg gac aag gtc ttc ccg tac gac cgc tac gag              1928
Thr Thr Tyr Gln Pro Met Asp Lys Val Phe Pro Tyr Asp Arg Tyr Glu
        520                 525                 530
```

```
                                                              -continued ggc atc aag atc cac gac tgg gac aag tgg gtc gac ccg ttc cgc ctg         1976
Gly Ile Lys Ile His Asp Trp Asp Lys Trp Val Asp Pro Phe Arg Leu
        535                 540                 545 acg atg gat gcg tac tgg aaa tac cag ggc gag aag gaa aag aag ctg         2024
Thr Met Asp Ala Tyr Trp Lys Tyr Gln Gly Glu Lys Glu Lys Lys Leu
550                 555                 560 tac gcg gtg atc gac gcg ttc acg cag aac aac gcg ttc ctc ggc gtg         2072
Tyr Ala Val Ile Asp Ala Phe Thr Gln Asn Asn Ala Phe Leu Gly Val
565                 570                 575                 580 agc gac gcc cgc tac atc aac gcg ctg aag ctg ttc ctc cag ggc gtg         2120
Ser Asp Ala Arg Tyr Ile Asn Ala Leu Lys Leu Phe Leu Gln Gly Val
                585                 590                 595 acg ccg ctc gaa tac ctc gcg cac cgc ggc ttc gcg cat gtc ggc cgg         2168
Thr Pro Leu Glu Tyr Leu Ala His Arg Gly Phe Ala His Val Gly Arg
            600                 605                 610 cac ttc acc ggc gag ggc gcg cgc atc gcg tgc cag atg cag tcg atc         2216
His Phe Thr Gly Glu Gly Ala Arg Ile Ala Cys Gln Met Gln Ser Ile
        615                 620                 625 gac gag ctg cgg cac tac cag acc gaa acg cat gcg atg tcg acg tac         2264
Asp Glu Leu Arg His Tyr Gln Thr Glu Thr His Ala Met Ser Thr Tyr
630                 635                 640 aac aag ttc ttc aac ggg ttc cat cac tcg aac cag tgg ttc gac cgc         2312
Asn Lys Phe Phe Asn Gly Phe His His Ser Asn Gln Trp Phe Asp Arg
645                 650                 655                 660 gtg tgg tac ctg tcg gtg ccg aag tcg ttc ttc gag gac gcg tat tcg         2360
Val Trp Tyr Leu Ser Val Pro Lys Ser Phe Phe Glu Asp Ala Tyr Ser
                665                 670                 675 tcg ggg ccg ttc gag ttc ctg acc gcg gtc agc ttc tcg ttc gaa tac         2408
Ser Gly Pro Phe Glu Phe Leu Thr Ala Val Ser Phe Ser Phe Glu Tyr
            680                 685                 690 gtg ctg acg aac ctg ctg ttc gtg ccg ttc atg tcg ggc gcc gcc tac         2456
Val Leu Thr Asn Leu Leu Phe Val Pro Phe Met Ser Gly Ala Ala Tyr
        695                 700                 705 aac ggt gac atg tcg acc gtc acg ttc ggc ttc tcc gcg cag tcg gac         2504
Asn Gly Asp Met Ser Thr Val Thr Phe Gly Phe Ser Ala Gln Ser Asp
710                 715                 720 gaa tcg cgt cac atg acg ctc ggc atc gaa tgc atc aag ttc ctg ctc         2552
Glu Ser Arg His Met Thr Leu Gly Ile Glu Cys Ile Lys Phe Leu Leu
725                 730                 735                 740 gaa cag gac ccg gac aac gtg ccg atc gtg cag cgc tgg atc gac aag         2600
Glu Gln Asp Pro Asp Asn Val Pro Ile Val Gln Arg Trp Ile Asp Lys
                745                 750                 755 tgg ttc tgg cgc ggc tac cgg ctg ctg acg ctg gtc gcg atg atg atg         2648
Trp Phe Trp Arg Gly Tyr Arg Leu Leu Thr Leu Val Ala Met Met Met
            760                 765                 770 gac tac atg cag ccc aag cgc gtg atg agc tgg cgc gag tcg tgg gag         2696
Asp Tyr Met Gln Pro Lys Arg Val Met Ser Trp Arg Glu Ser Trp Glu
        775                 780                 785 atg tac gcc gag cag aac ggc ggc gcg ctg ttc aag gat ctc gcg cgc         2744
Met Tyr Ala Glu Gln Asn Gly Gly Ala Leu Phe Lys Asp Leu Ala Arg
790                 795                 800 tac ggc att cgc gag ccg aag ggc tgg cag gac gcc tgc gaa ggc aag         2792
Tyr Gly Ile Arg Glu Pro Lys Gly Trp Gln Asp Ala Cys Glu Gly Lys
805                 810                 815                 820 gat cac atc agc cac cag gcg tgg tcg acg ttc tac ggc ttc aac gcg         2840
Asp His Ile Ser His Gln Ala Trp Ser Thr Phe Tyr Gly Phe Asn Ala
                825                 830                 835 gcc tcg gcg ttc cac acc tgg gtg ccg acc gaa gac gaa atg ggc tgg         2888
Ala Ser Ala Phe His Thr Trp Val Pro Thr Glu Asp Glu Met Gly Trp
            840                 845                 850
```

```
ctg tcg gcg aag tat ccc gac tcg ttc gac cgc tac tac cgc ccg cgc         2936
Leu Ser Ala Lys Tyr Pro Asp Ser Phe Asp Arg Tyr Tyr Arg Pro Arg
        855                 860                 865 ttc gat cac tgg ggc gag cag gcc agg gcc ggc aac cgc ttc tac atg         2984
Phe Asp His Trp Gly Glu Gln Ala Arg Ala Gly Asn Arg Phe Tyr Met
870                 875                 880 aag acg ctg ccg atg ctg tgc cag acg tgc cag atc ccg atg ctg ttc         3032
Lys Thr Leu Pro Met Leu Cys Gln Thr Cys Gln Ile Pro Met Leu Phe
885                 890                 895                 900 acc gag ccg ggc aac ccg acg aag atc ggc gcg cgc gaa tcg aac tac         3080
Thr Glu Pro Gly Asn Pro Thr Lys Ile Gly Ala Arg Glu Ser Asn Tyr
            905                 910                 915 ctc ggc aac aag ttc cac ttc tgc agc gac cac tgc aag gac atc ttc         3128
Leu Gly Asn Lys Phe His Phe Cys Ser Asp His Cys Lys Asp Ile Phe
        920                 925                 930 gat cac gag ccg cag aaa tac gtg cag gcg tgg ctg ccg gtg cac cag         3176
Asp His Glu Pro Gln Lys Tyr Val Gln Ala Trp Leu Pro Val His Gln
    935                 940                 945 atc cat cag ggc aac tgc ttc ccg ccc gat gcg gac ccg ggc gcg gag         3224
Ile His Gln Gly Asn Cys Phe Pro Pro Asp Ala Asp Pro Gly Ala Glu
950                 955                 960 ggc ttc gat ccg ctc gcc gcg gtg ctc gac tac tac gcg gtg acg atg         3272
Gly Phe Asp Pro Leu Ala Ala Val Leu Asp Tyr Tyr Ala Val Thr Met
965                 970                 975                 980 ggc cgc gac aac ctc gat ttc gac ggc tcg gaa gac cag aag aac ttc         3320
Gly Arg Asp Asn Leu Asp Phe Asp Gly Ser Glu Asp Gln Lys Asn Phe
            985                 990                 995 gcg gcg tgg cgc ggc cag gcc acg cgc aac tgacccgcaa cgacaagcaa           3370
Ala Ala Trp Arg Gly Gln Ala Thr Arg Asn
        1000                1005 tcttgacgag ggcccgcgaa gcgccgatgc gcgaacgcgg gccgacagga gacaaac          3427 atg gcc gtc atc gcg ctc aaa ccc tac gac ttc ccg gtg aag gat gcc         3475
Met Ala Val Ile Ala Leu Lys Pro Tyr Asp Phe Pro Val Lys Asp Ala
            1010                1015                1020 gtc gag aag ttt ccg gcg ccg ctg ctc tac gtg tgc tgg gaa aac cat         3523
Val Glu Lys Phe Pro Ala Pro Leu Leu Tyr Val Cys Trp Glu Asn His
        1025                1030                1035 ctg atg ttc ccg gcg ccg ttc tgc ctg ccg ctg ccg ccc gac atg ccg         3571
Leu Met Phe Pro Ala Pro Phe Cys Leu Pro Leu Pro Pro Asp Met Pro
    1040                1045                1050 ttc ggc gcg ctg gcc ggc gac gtg ctg ccg ccc gtc tac ggc tat cac         3619
Phe Gly Ala Leu Ala Gly Asp Val Leu Pro Pro Val Tyr Gly Tyr His
1055                1060                1065                1070 ccc gac ttc gcg aag atc gac tgg gat cgc gtc gag tgg ttc cgg tcg         3667
Pro Asp Phe Ala Lys Ile Asp Trp Asp Arg Val Glu Trp Phe Arg Ser
            1075                1080                1085 ggc gag ccg tgg gcg ccg gac ccg gcg aag agc ctg gcc ggc aac ggc         3715
Gly Glu Pro Trp Ala Pro Asp Pro Ala Lys Ser Leu Ala Gly Asn Gly
        1090                1095                1100 ctc ggg cac aag gac ctg atc agc ttc cgc acg ccc ggc ctc gac ggc         3763
Leu Gly His Lys Asp Leu Ile Ser Phe Arg Thr Pro Gly Leu Asp Gly
    1105                1110                1115 ctc ggc ggc gcg agc ttc tgaccgccac gcggacgagc gaaccatc atg agc          3815
Leu Gly Gly Ala Ser Phe                                 Met Ser
1120                                                    1125 cac caa ctt acc atc gag ccg ctg ggc gtc acg atc gag gtc gag gaa         3863
His Gln Leu Thr Ile Glu Pro Leu Gly Val Thr Ile Glu Val Glu Glu
            1130                1135                1140
```

-continued

| | |
|---|---|
| gga cag acg atg ctc gat gcc gcg ctg cgc cag ggc atc tac att ccg<br>Gly Gln Thr Met Leu Asp Ala Ala Leu Arg Gln Gly Ile Tyr Ile Pro<br>　　　1145　　　　　　　1150　　　　　　　1155 | 3911 |
| cac gcg tgc tgt cac ggg ctg tgc ggc acc tgc aag gtc gcc gtg ctc<br>His Ala Cys Cys His Gly Leu Cys Gly Thr Cys Lys Val Ala Val Leu<br>1160　　　　　　　1165　　　　　　　1170 | 3959 |
| gac ggc gag acc gat ccc ggc gat gcg aac ccg ttc gcg ctg atg gat<br>Asp Gly Glu Thr Asp Pro Gly Asp Ala Asn Pro Phe Ala Leu Met Asp<br>1175　　　　　　　1180　　　　　　　1185　　　　　　　1190 | 4007 |
| ttc gag cgc gag gaa ggc aag gcg ctc gcg tgc tgc gcg acg ctg cag<br>Phe Glu Arg Glu Glu Gly Lys Ala Leu Ala Cys Cys Ala Thr Leu Gln<br>　　　1195　　　　　　　1200　　　　　　　1205 | 4055 |
| gcc gac acc gtg atc gag gcc gac gtc gac gag gag ccg gat gcg gaa<br>Ala Asp Thr Val Ile Glu Ala Asp Val Asp Glu Glu Pro Asp Ala Glu<br>1210　　　　　　　1215　　　　　　　1220 | 4103 |
| atc atc ccg gtc agg gac ttc gcg gcc gac gtc acg cgc atc gaa cag<br>Ile Ile Pro Val Arg Asp Phe Ala Ala Asp Val Thr Arg Ile Glu Gln<br>1225　　　　　　　1230　　　　　　　1235 | 4151 |
| ctc acg ccg acc atc aag tcg atc cgc ctg aag ctg tcg cag ccg atc<br>Leu Thr Pro Thr Ile Lys Ser Ile Arg Leu Lys Leu Ser Gln Pro Ile<br>　　　1240　　　　　　　1245　　　　　　　1250 | 4199 |
| cgc ttc cag gcg ggc cag tac gtg cag ctc gag att ccc ggc ctc ggg<br>Arg Phe Gln Ala Gly Gln Tyr Val Gln Leu Glu Ile Pro Gly Leu Gly<br>1255　　　　　　　1260　　　　　　　1265　　　　　　　1270 | 4247 |
| cag agc cgc gcg ttc tcg atc gcg aac gcg ccg gcc gac gtc gcg gcc<br>Gln Ser Arg Ala Phe Ser Ile Ala Asn Ala Pro Ala Asp Val Ala Ala<br>　　　1275　　　　　　　1280　　　　　　　1285 | 4295 |
| acc ggc gag atc gaa ctg aac gtg cgg cag gtg ccg ggc ggg ctc ggc<br>Thr Gly Glu Ile Glu Leu Asn Val Arg Gln Val Pro Gly Gly Leu Gly<br>1290　　　　　　　1295　　　　　　　1300 | 4343 |
| acg ggc tac ctg cac gag caa ctg gcg acg ggc gag cgc gtg cgc ctg<br>Thr Gly Tyr Leu His Glu Gln Leu Ala Thr Gly Glu Arg Val Arg Leu<br>1305　　　　　　　1310　　　　　　　1315 | 4391 |
| tcg ggc ccg tac ggc cgc ttc ttc gtg cgt cgc tcg gcc gcg cgg ccg<br>Ser Gly Pro Tyr Gly Arg Phe Phe Val Arg Arg Ser Ala Ala Arg Pro<br>　　　1320　　　　　　　1325　　　　　　　1330 | 4439 |
| atg atc ttc atg gcc ggc ggg tcg ggg ctg tcg agc ccg cgc tcg atg<br>Met Ile Phe Met Ala Gly Gly Ser Gly Leu Ser Ser Pro Arg Ser Met<br>1335　　　　　　　1340　　　　　　　1345　　　　　　　1350 | 4487 |
| atc gcg gac ctg ctc gca agc ggc gtc acc gcg ccg atc acg ctg gtc<br>Ile Ala Asp Leu Leu Ala Ser Gly Val Thr Ala Pro Ile Thr Leu Val<br>　　　1355　　　　　　　1360　　　　　　　1365 | 4535 |
| tac ggt cag cgc agc gcg cag gag ctc tac tac cac gac gaa ttc cgc<br>Tyr Gly Gln Arg Ser Ala Gln Glu Leu Tyr Tyr His Asp Glu Phe Arg<br>1370　　　　　　　1375　　　　　　　1380 | 4583 |
| gcg ctg gcc gaa cgc cat ccg aac ttc acg tac gtg ccg gcg ctg tcc<br>Ala Leu Ala Glu Arg His Pro Asn Phe Thr Tyr Val Pro Ala Leu Ser<br>1385　　　　　　　1390　　　　　　　1395 | 4631 |
| gaa ggc gca ccg cac gcg ggc ggc gac gtc gcg caa ggg ttc gtg cac<br>Glu Gly Ala Pro His Ala Gly Gly Asp Val Ala Gln Gly Phe Val His<br>1400　　　　　　　1405　　　　　　　1410 | 4679 |
| gac gtc gcg aag gca cat ttc ggc ggc gac ttc tcc ggg cac cag gcg<br>Asp Val Ala Lys Ala His Phe Gly Gly Asp Phe Ser Gly His Gln Ala<br>1415　　　　　　　1420　　　　　　　1425　　　　　　　1430 | 4727 |
| tac ctg tgc ggg ccg ccc gcg atg atc gac gcg tgc atc acg acg ctg<br>Tyr Leu Cys Gly Pro Pro Ala Met Ile Asp Ala Cys Ile Thr Thr Leu<br>　　　1435　　　　　　　1440　　　　　　　1445 | 4775 |
| atg cag ggg cgc ctg ttc gag cgc gac atc tat cac gag aag ttc atc<br>Met Gln Gly Arg Leu Phe Glu Arg Asp Ile Tyr His Glu Lys Phe Ile<br>1450　　　　　　　1455　　　　　　　1460 | 4823 |

-continued

```
tcg gcg gcc gac gcg caa cag acg cgc agc ccg ctg ttc cgg cgg gtg      4871
Ser Ala Ala Asp Ala Gln Gln Thr Arg Ser Pro Leu Phe Arg Arg Val
1465                1470                1475 tga  atg gac gcg ggc cgc gta tgc ggg acg gtc acg atc gcg cag acc     4920
     Met Asp Ala Gly Arg Val Cys Gly Thr Val Thr Ile Ala Gln Thr
         1480                1485                1490 gac gag cgc tat gcg tgc gtg tcc ggc gag tcg ctg ctg gcc ggc atg      4968
Asp Glu Arg Tyr Ala Cys Val Ser Gly Glu Ser Leu Leu Ala Gly Met
1495                1500                1505 gcg aaa ctc ggc cgg cgc ggc att ccg gtc ggc tgc ctg aac ggc ggg      5016
Ala Lys Leu Gly Arg Arg Gly Ile Pro Val Gly Cys Leu Asn Gly Gly
1510                1515                1520                1525 tgc ggc gtg tgc aag gtg cgc gtg ctg cgc ggt gcg gtg cgc aag ctc      5064
Cys Gly Val Cys Lys Val Arg Val Leu Arg Gly Ala Val Arg Lys Leu
                1530                1535                1540 ggg ccg atc agc cgt gcc cat gtg agc gcg gaa gaa gag aac gac ggc      5112
Gly Pro Ile Ser Arg Ala His Val Ser Ala Glu Glu Glu Asn Asp Gly
1545                1550                1555 tac gcg ctt gcg tgc cgc gtc gtg ccg gac ggc gac gtc gaa ctc gaa      5160
Tyr Ala Leu Ala Cys Arg Val Val Pro Asp Gly Asp Val Glu Leu Glu
1560                1565                1570 gtg gcc ggc cgg ctc agg aag ccg ttc ttc tgc ggc atg gca tgt gcc      5208
Val Ala Gly Arg Leu Arg Lys Pro Phe Phe Cys Gly Met Ala Cys Ala
1575                1580                1585 ggc acg gcg gcg atc aac aag taaccaggag gagactcacc atgggtgtga         5259
Gly Thr Ala Ala Ile Asn Lys
1590            1595 tgcgtattgg tcatgtcagt ctgaaggtga tggacatgga agcggcgctg cgtcattacg    5319
tacgcgtgct cggcatgcag gaaacgatgc gcgacgcggc gggcaacgtc tacctgaaat    5379
gctgggacga atgggacaag tattcgctga tcctgtcgcc gtccgatcag gcggggctca    5439
agcatgccgc ctacaaggtc gagcacgacg ccgatctgga tgcgctgcag cagcgcatcg    5499
aagcgtacgg gatcgcgacc gagatgctgc ccgaaggcgc gctgccggcg gtcggccgcc    5559
aactgcggtt cctgctgccg agcggccatg aactgcggct gttcgcgaag aaggcgctgg    5619
tgggcaccgc ggtcggctcg ctgaaccccg atccgtggcc cgacgacatt ccgggctcgg    5679
ccgtgcactg gctcgaccac tgcctgctga tgtgcgaact gaacccggag gccggcgtga    5739
accgcgtcga ggagaacacg cgcttcatgg ccgagtgtct cgacttccat ctggccgagc    5799
aggtgatggt cggcccgggc aacacgatc                                      5828
```

<210> SEQ ID NO 2
<211> LENGTH: 70
<212> TYPE: PRT
<213> ORGANISM: Burkholderia cepacia
<220> FEATURE:
<223> OTHER INFORMATION: TomK polypeptide

<400> SEQUENCE: 2

```
Met Asn Gln His Pro Thr Asp Leu Ser Pro Phe Asp Pro Gly Arg Lys
1               5                   10                  15

Cys Val Arg Val Thr Gly Thr Asn Ala Arg Gly Phe Val Glu Phe Glu
            20                  25                  30

Leu Ser Ile Gly Gly Ala Pro Glu Leu Cys Val Glu Leu Thr Leu Ser
        35                  40                  45

Pro Ala Ala Phe Asp Ala Phe Cys Arg Glu Gln Gln Val Thr Arg Leu
    50                  55                  60
```

-continued

Asp Val Glu Ala Asn Pro
 65                  70

<210> SEQ ID NO 3
<211> LENGTH: 331
<212> TYPE: PRT
<213> ORGANISM: Burkholderia cepacia
<220> FEATURE:
<223> OTHER INFORMATION: TomL polypeptide

<400> SEQUENCE: 3

Met Thr Ile Glu Leu Lys Thr Val Asp Ile Lys Pro Leu Arg His Thr
  1               5                  10                  15

Phe Ala His Val Ala Gln Asn Ile Gly Gly Asp Lys Thr Ala Thr Arg
             20                  25                  30

Tyr Gln Glu Gly Met Met Gly Ala Gln Pro Gln Glu Asn Phe His Tyr
         35                  40                  45

Arg Pro Thr Trp Asp Pro Asp Tyr Glu Ile Phe Asp Pro Ser Arg Ser
     50                  55                  60

Ala Ile Arg Met Ala Asn Trp Tyr Ala Leu Lys Asp Pro Arg Gln Phe
 65                  70                  75                  80

Tyr Tyr Ala Ser Trp Ala Thr Thr Arg Ala Arg Gln Gln Asp Ala Met
                 85                  90                  95

Glu Ser Asn Phe Glu Phe Val Glu Ser Arg Arg Met Ile Gly Leu Met
            100                 105                 110

Arg Asp Asp Val Ala Ala Arg Ala Leu Asp Val Leu Val Pro Leu Arg
        115                 120                 125

His Ala Ala Trp Gly Ala Asn Met Asn Asn Ala Gln Ile Cys Ala Leu
    130                 135                 140

Gly Tyr Gly Thr Val Phe Thr Ala Pro Ala Met Phe His Ala Met Asp
145                 150                 155                 160

Asn Leu Gly Val Ala Gln Tyr Leu Thr Arg Leu Ala Leu Ala Met Ala
                165                 170                 175

Glu Pro Asp Val Leu Glu Ala Ala Lys Ala Thr Trp Thr Arg Asp Ala
            180                 185                 190

Ala Trp Gln Pro Leu Arg Arg Tyr Val Glu Asp Thr Leu Val Val Ala
        195                 200                 205

Asp Pro Val Glu Leu Phe Ile Ala Gln Asn Leu Ala Leu Asp Gly Leu
    210                 215                 220

Leu Tyr Pro Leu Val Tyr Asp Arg Phe Val Asp Glu Arg Ile Ala Leu
225                 230                 235                 240

Glu Gly Gly Ser Ala Val Ala Met Leu Thr Ala Phe Met Pro Glu Trp
                245                 250                 255

His Thr Glu Ser Asn Arg Trp Ile Asp Ala Val Val Lys Thr Met Ala
            260                 265                 270

Ala Glu Ser Asp Asp Asn Arg Ala Leu Leu Ala Arg Trp Thr Arg Asp
        275                 280                 285

Trp Ser Ala Arg Ala Glu Ala Ala Leu Ala Pro Val Ala Ala Arg Ala
    290                 295                 300

Leu Gln Asp Ala Gly Arg Ala Ala Leu Asp Glu Val Arg Glu Gln Phe
305                 310                 315                 320

His Ala Arg Ala Ala Arg Leu Gly Ile Ala Leu
                325                 330

<210> SEQ ID NO 4
<211> LENGTH: 89

-continued

```
<212> TYPE: PRT
<213> ORGANISM: Burkholderia cepacia
<220> FEATURE:
<223> OTHER INFORMATION: TomM polypeptide

<400> SEQUENCE: 4

Met Ser Asn Val Phe Ile Ala Phe Gln Ala Asn Glu Asp Ser Arg Pro
 1               5                  10                  15

Ile Val Asp Ala Ile Val Ala Asp Asn Pro Arg Ala Val Val Val Glu
            20                  25                  30

Ser Pro Gly Met Val Lys Ile Asp Ala Pro Asp Arg Leu Thr Ile Arg
        35                  40                  45

Arg Glu Thr Ile Glu Glu Leu Thr Gly Thr Arg Phe Asp Leu Gln Gln
50                  55                  60

Leu Gln Val Asn Leu Ile Thr Leu Ser Gly His Ile Asp Glu Asp Asp
65                  70                  75                  80

Asp Glu Phe Thr Leu Ser Trp Ser His
                85

<210> SEQ ID NO 5
<211> LENGTH: 516
<212> TYPE: PRT
<213> ORGANISM: Burkholderia cepacia
<220> FEATURE:
<223> OTHER INFORMATION: TomN polypeptide

<400> SEQUENCE: 5

Met Asp Thr Pro Thr Leu Lys Lys Leu Gly Leu Lys Asp Arg Tyr
 1               5                  10                  15

Ala Ala Met Thr Arg Gly Leu Gly Trp Glu Thr Thr Tyr Gln Pro Met
            20                  25                  30

Asp Lys Val Phe Pro Tyr Asp Arg Tyr Glu Gly Ile Lys Ile His Asp
        35                  40                  45

Trp Asp Lys Trp Val Asp Pro Phe Arg Leu Thr Met Asp Ala Tyr Trp
50                  55                  60

Lys Tyr Gln Gly Glu Lys Glu Lys Lys Leu Tyr Ala Val Ile Asp Ala
65                  70                  75                  80

Phe Thr Gln Asn Asn Ala Phe Leu Gly Val Ser Asp Ala Arg Tyr Ile
                85                  90                  95

Asn Ala Leu Lys Leu Phe Leu Gln Gly Val Thr Pro Leu Glu Tyr Leu
            100                 105                 110

Ala His Arg Gly Phe Ala His Val Gly Arg His Phe Thr Gly Glu Gly
        115                 120                 125

Ala Arg Ile Ala Cys Gln Met Gln Ser Ile Asp Glu Leu Arg His Tyr
130                 135                 140

Gln Thr Glu Thr His Ala Met Ser Thr Tyr Asn Lys Phe Phe Asn Gly
145                 150                 155                 160

Phe His His Ser Asn Gln Trp Phe Asp Arg Val Trp Tyr Leu Ser Val
                165                 170                 175

Pro Lys Ser Phe Phe Glu Asp Ala Tyr Ser Ser Gly Pro Phe Glu Phe
            180                 185                 190

Leu Thr Ala Val Ser Phe Ser Phe Glu Tyr Val Leu Thr Asn Leu Leu
        195                 200                 205

Phe Val Pro Phe Met Ser Gly Ala Ala Tyr Asn Gly Asp Met Ser Thr
210                 215                 220

Val Thr Phe Gly Phe Ser Ala Gln Ser Asp Glu Ser Arg His Met Thr
225                 230                 235                 240
```

```
Leu Gly Ile Glu Cys Ile Lys Phe Leu Leu Glu Gln Asp Pro Asp Asn
                245                 250                 255

Val Pro Ile Val Gln Arg Trp Ile Asp Lys Trp Phe Trp Arg Gly Tyr
            260                 265                 270

Arg Leu Leu Thr Leu Val Ala Met Met Met Asp Tyr Met Gln Pro Lys
        275                 280                 285

Arg Val Met Ser Trp Arg Glu Ser Trp Glu Met Tyr Ala Glu Gln Asn
    290                 295                 300

Gly Gly Ala Leu Phe Lys Asp Leu Ala Arg Tyr Gly Ile Arg Glu Pro
305                 310                 315                 320

Lys Gly Trp Gln Asp Ala Cys Glu Gly Lys Asp His Ile Ser His Gln
                325                 330                 335

Ala Trp Ser Thr Phe Tyr Gly Phe Asn Ala Ala Ser Ala Phe His Thr
            340                 345                 350

Trp Val Pro Thr Glu Asp Glu Met Gly Trp Leu Ser Ala Lys Tyr Pro
        355                 360                 365

Asp Ser Phe Asp Arg Tyr Tyr Arg Pro Arg Phe Asp His Trp Gly Glu
    370                 375                 380

Gln Ala Arg Ala Gly Asn Arg Phe Tyr Met Lys Thr Leu Pro Met Leu
385                 390                 395                 400

Cys Gln Thr Cys Gln Ile Pro Met Leu Phe Thr Glu Pro Gly Asn Pro
                405                 410                 415

Thr Lys Ile Gly Ala Arg Glu Ser Asn Tyr Leu Gly Asn Lys Phe His
            420                 425                 430

Phe Cys Ser Asp His Cys Lys Asp Ile Phe Asp His Glu Pro Gln Lys
        435                 440                 445

Tyr Val Gln Ala Trp Leu Pro Val His Gln Ile His Gln Gly Asn Cys
    450                 455                 460

Phe Pro Pro Asp Ala Asp Pro Gly Ala Glu Gly Phe Asp Pro Leu Ala
465                 470                 475                 480

Ala Val Leu Asp Tyr Tyr Ala Val Thr Met Gly Arg Asp Asn Leu Asp
                485                 490                 495

Phe Asp Gly Ser Glu Asp Gln Lys Asn Phe Ala Ala Trp Arg Gly Gln
            500                 505                 510

Ala Thr Arg Asn
        515
```

<210> SEQ ID NO 6
<211> LENGTH: 118
<212> TYPE: PRT
<213> ORGANISM: Burkholderia cepacia
<220> FEATURE:
<223> OTHER INFORMATION: TomO polypeptide

<400> SEQUENCE: 6

```
Met Ala Val Ile Ala Leu Lys Pro Tyr Asp Phe Pro Val Lys Asp Ala
 1               5                  10                  15

Val Glu Lys Phe Pro Ala Pro Leu Leu Tyr Val Cys Trp Glu Asn His
            20                  25                  30

Leu Met Phe Pro Ala Pro Phe Cys Leu Pro Leu Pro Pro Asp Met Pro
        35                  40                  45

Phe Gly Ala Leu Ala Gly Asp Val Leu Pro Pro Val Tyr Gly Tyr His
    50                  55                  60

Pro Asp Phe Ala Lys Ile Asp Trp Asp Arg Val Glu Trp Phe Arg Ser
65                  70                  75                  80
```

-continued

```
Gly Glu Pro Trp Ala Pro Asp Pro Ala Lys Ser Leu Ala Gly Asn Gly
                85                  90                  95

Leu Gly His Lys Asp Leu Ile Ser Phe Arg Thr Pro Gly Leu Asp Gly
            100                 105                 110

Leu Gly Gly Ala Ser Phe
        115

<210> SEQ ID NO 7
<211> LENGTH: 354
<212> TYPE: PRT
<213> ORGANISM: Burkholderia cepacia
<220> FEATURE:
<223> OTHER INFORMATION: TomP polypeptide

<400> SEQUENCE: 7

Met Ser His Gln Leu Thr Ile Glu Pro Leu Gly Val Thr Ile Glu Val
  1               5                  10                  15

Glu Glu Gly Gln Thr Met Leu Asp Ala Ala Leu Arg Gln Gly Ile Tyr
             20                  25                  30

Ile Pro His Ala Cys Cys His Gly Leu Cys Gly Thr Cys Lys Val Ala
         35                  40                  45

Val Leu Asp Gly Glu Thr Asp Pro Gly Asp Ala Asn Pro Phe Ala Leu
 50                  55                  60

Met Asp Phe Glu Arg Glu Gly Lys Ala Leu Ala Cys Cys Ala Thr
 65                  70                  75                  80

Leu Gln Ala Asp Thr Val Ile Glu Ala Asp Val Asp Glu Glu Pro Asp
                 85                  90                  95

Ala Glu Ile Ile Pro Val Arg Asp Phe Ala Ala Asp Val Thr Arg Ile
            100                 105                 110

Glu Gln Leu Thr Pro Thr Ile Lys Ser Ile Arg Leu Lys Leu Ser Gln
        115                 120                 125

Pro Ile Arg Phe Gln Ala Gly Gln Tyr Val Gln Leu Glu Ile Pro Gly
130                 135                 140

Leu Gly Gln Ser Arg Ala Phe Ser Ile Ala Asn Ala Pro Ala Asp Val
145                 150                 155                 160

Ala Ala Thr Gly Glu Ile Glu Leu Asn Val Arg Gln Val Pro Gly Gly
                165                 170                 175

Leu Gly Thr Gly Tyr Leu His Glu Gln Leu Ala Thr Gly Glu Arg Val
            180                 185                 190

Arg Leu Ser Gly Pro Tyr Gly Arg Phe Val Arg Arg Ser Ala Ala
        195                 200                 205

Arg Pro Met Ile Phe Met Ala Gly Gly Ser Gly Leu Ser Ser Pro Arg
210                 215                 220

Ser Met Ile Ala Asp Leu Leu Ala Ser Gly Val Thr Ala Pro Ile Thr
225                 230                 235                 240

Leu Val Tyr Gly Gln Arg Ser Ala Gln Glu Leu Tyr Tyr His Asp Glu
                245                 250                 255

Phe Arg Ala Leu Ala Glu Arg His Pro Asn Phe Thr Tyr Val Pro Ala
            260                 265                 270

Leu Ser Glu Gly Ala Pro His Ala Gly Asp Val Ala Gln Gly Phe
        275                 280                 285

Val His Asp Val Ala Lys Ala His Phe Gly Gly Asp Phe Ser Gly His
    290                 295                 300

Gln Ala Tyr Leu Cys Gly Pro Pro Ala Met Ile Asp Ala Cys Ile Thr
305                 310                 315                 320
```

```
Thr Leu Met Gln Gly Arg Leu Phe Glu Arg Asp Ile Tyr His Glu Lys
            325                 330                 335

Phe Ile Ser Ala Ala Asp Ala Gln Gln Thr Arg Ser Pro Leu Phe Arg
            340                 345                 350

Arg Val

<210> SEQ ID NO 8
<211> LENGTH: 118
<212> TYPE: PRT
<213> ORGANISM: Burkholderia cepacia
<220> FEATURE:
<223> OTHER INFORMATION: TomQ polypeptide

<400> SEQUENCE: 8

Met Asp Ala Gly Arg Val Cys Gly Thr Val Thr Ile Ala Gln Thr Asp
  1               5                  10                  15

Glu Arg Tyr Ala Cys Val Ser Gly Glu Ser Leu Leu Ala Gly Met Ala
             20                  25                  30

Lys Leu Gly Arg Arg Gly Ile Pro Val Gly Cys Leu Asn Gly Gly Cys
         35                  40                  45

Gly Val Cys Lys Val Arg Val Leu Arg Gly Ala Val Arg Lys Leu Gly
     50                  55                  60

Pro Ile Ser Arg Ala His Val Ser Ala Glu Glu Asn Asp Gly Tyr
 65                  70                  75                  80

Ala Leu Ala Cys Arg Val Val Pro Asp Gly Asp Val Glu Leu Glu Val
                 85                  90                  95

Ala Gly Arg Leu Arg Lys Pro Phe Phe Cys Gly Met Ala Cys Ala Gly
            100                 105                 110

Thr Ala Ala Ile Asn Lys
        115

<210> SEQ ID NO 9
<211> LENGTH: 36
<212> TYPE: DNA
<213> ORGANISM: Artificial Sequence
<220> FEATURE:
<223> OTHER INFORMATION: Description of Artificial Sequence: Designed
      PCR primer

<400> SEQUENCE: 9
agtccgccat ggaggcgaca ccgatcatga atcagc                           36

<210> SEQ ID NO 10
<211> LENGTH: 34
<212> TYPE: DNA
<213> ORGANISM: Artificial Sequence
<220> FEATURE:
<223> OTHER INFORMATION: Description of Artificial Sequence: Designed
      PCR primer

<400> SEQUENCE: 10
caccgaccat ggatcagcac cccaccgatc tttc                             34

<210> SEQ ID NO 11
<211> LENGTH: 34
<212> TYPE: DNA
<213> ORGANISM: Artificial Sequence
<220> FEATURE:
<223> OTHER INFORMATION: Description of Artificial Sequence: Designed
      PCR primer

<400> SEQUENCE: 11
```

```
tgccgccttc catgggttct gccgcgaaca gcag                    34

<210> SEQ ID NO 12
<211> LENGTH: 39
<212> TYPE: DNA
<213> ORGANISM: Artificial Sequence
<220> FEATURE:
<223> OTHER INFORMATION: Description of Artificial Sequence: Designed
      PCR primer

<400> SEQUENCE: 12
agcaagccat ggccatcgag ctgaagacag tcgacatca               39

<210> SEQ ID NO 13
<211> LENGTH: 35
<212> TYPE: DNA
<213> ORGANISM: Artificial Sequence
<220> FEATURE:
<223> OTHER INFORMATION: Description of Artificial Sequence: Designed
      PCR primer

<400> SEQUENCE: 13
ccgaccatca cctgctcggc cagatggaag tcgag                   35
```